(12) United States Patent
Takatsuji

(10) Patent No.: US 11,311,178 B2
(45) Date of Patent: Apr. 26, 2022

(54) ENDOSCOPE

(71) Applicant: OLYMPUS CORPORATION, Tokyo (JP)

(72) Inventor: Kenji Takatsuji, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 491 days.

(21) Appl. No.: 16/373,841

(22) Filed: Apr. 3, 2019

(65) Prior Publication Data

US 2019/0223691 A1 Jul. 25, 2019

Related U.S. Application Data

(63) Continuation of application No. PCT/JP2017/029958, filed on Aug. 22, 2017.

(30) Foreign Application Priority Data

Dec. 26, 2016 (JP) .............................. JP2016-251714

(51) Int. Cl.
*A61B 1/00* (2006.01)
*A61B 1/005* (2006.01)
(Continued)

(52) U.S. Cl.
CPC .............. *A61B 1/0052* (2013.01); *A61B 1/00* (2013.01); *A61B 1/005* (2013.01); *A61B 1/008* (2013.01);
(Continued)

(58) Field of Classification Search
None
See application file for complete search history.

(56) References Cited

U.S. PATENT DOCUMENTS

2003/0092965 A1* 5/2003 Konomura ......... G02B 23/2476
600/146
2004/0267093 A1* 12/2004 Miyagi .............. A61B 1/00039
600/146

(Continued)

FOREIGN PATENT DOCUMENTS

JP H02-215436 A 8/1990
JP H04-71523 A 3/1992
(Continued)

OTHER PUBLICATIONS

International Search Report dated Nov. 7, 2017 issued in PCT/JP2017/029958.

*Primary Examiner* — Timothy J Neal
(74) *Attorney, Agent, or Firm* — Scully, Scott, Murphy & Presser, P.C.

(57) ABSTRACT

An endoscope includes a bending portion bendable in all directions including four directions: an up direction, a down direction, a left direction, and a right direction, a bending operation lever configured to bend the bending portion by being tilted, and a wire pulling mechanism provided integrally on the bending operation lever and including a lever tilting angle adjustment mechanism configured to set a first tilting angle at which the bending operation lever is tilted in order to bend the bending portion to at least one direction in the four directions by a predetermined bending angle and a second tilting angle at which the bending operation lever is tilted in order to bend the bending portion in a direction different from the at least one direction by a predetermined bending angle to different angles when the bending operation lever is tilted so as to bend the bending portion.

16 Claims, 17 Drawing Sheets

(51) Int. Cl.
    *A61B 1/008* (2006.01)
    *G02B 23/24* (2006.01)
    *A61B 1/05* (2006.01)
    *A61B 1/01* (2006.01)

(52) U.S. Cl.
    CPC ........ *A61B 1/0057* (2013.01); *G02B 23/2476* (2013.01); *A61B 1/01* (2013.01); *A61B 1/05* (2013.01)

(56) References Cited

U.S. PATENT DOCUMENTS

| | | | |
|---|---|---|---|
| 2008/0275303 A1* | 11/2008 | Koitabashi | G05G 5/04 600/146 |
| 2013/0331652 A1* | 12/2013 | Okamoto | A61B 1/0052 600/146 |
| 2014/0309625 A1* | 10/2014 | Okamoto | A61B 34/71 606/1 |
| 2016/0157699 A1 | 6/2016 | Okamoto | |
| 2016/0231556 A1* | 8/2016 | Yasunaga | G01D 11/16 |
| 2017/0196435 A1* | 7/2017 | Sato | G02B 23/2476 |
| 2017/0215697 A1* | 8/2017 | Hatano | A61B 1/0057 |
| 2017/0251906 A1* | 9/2017 | Hatano | A61B 1/0055 |
| 2017/0280973 A1* | 10/2017 | Hatano | A61B 1/0057 |

FOREIGN PATENT DOCUMENTS

| | | |
|---|---|---|
| JP | H09-010172 A | 1/1997 |
| JP | H09-094218 A | 4/1997 |
| JP | H09-173279 A | 7/1997 |
| JP | 2013-052078 A | 3/2013 |
| JP | 2015-198790 A | 11/2015 |
| JP | 2016-055041 A | 4/2016 |
| WO | WO 2015/050062 A1 | 4/2015 |

\* cited by examiner

ENDOSCOPE

CROSS REFERENCE TO RELATED APPLICATION

This application is a continuation application of PCT/JP2017/029958 filed on Aug. 22, 2017 and claims benefit of Japanese Application No. 2016-251714 filed in Japan on Dec. 26, 2016, the entire contents of which are incorporated herein by this reference.

BACKGROUND OF THE INVENTION

1. Field of the Invention

The present invention relates to an endoscope in which a bending portion provided on an insertion portion is bent in accordance with a tilting operation of a bending operation lever.

2. Description of the Related Art

Endoscopes are used in a medical field, or in an industrial field and the like. Some endoscopes have a bendable bending portion provided on an insertion portion for a purpose of improving an insertion performance of the insertion portion or for the purpose of improving an observation performance.

The bending portion is constituted to be bent in an up-down direction or in up-down and left-right directions by operating a bending operation device provided on an operation portion.

Japanese Patent Application Laid-Open Publication No. 09-094218 discloses an endoscope in which the bending portion is bent by pulling a bending operation wire. The insertion portion is configured by connecting a distal end portion, a bending portion configured to turnably connect a plurality of bending rings and bendable in up-down/left-right directions, and a flexible tube in order. Two angle knobs are provided as the bending operation device in the operation portion. One of them is an up-down direction turnable angle knob configured to bend the bending portion in the up-down direction, while the other is a left-right direction turnable angle knob configured to bend the bending portion in the left-right direction.

According to the endoscope, the bending portion is bent to an up direction or to a down direction by turning the up-down direction angle knob so as to move an up bending wire and a down bending wire. On the other hand, the bending portion is bent to a left direction or to a right direction by turning the left-right direction angle knob so as to move a left bending wire and a right bending wire.

Japanese Patent Application Laid-Open Publication No. 09-173279 discloses an endoscope in which an up-down bending lever and a left-right bending lever as the bending operation device are provided instead of the up-down angle knob and the left-right angle knob. According to the endoscope, the bending portion is bent to the up direction or to the down direction by the turning operation of the up-down bending lever and is bent to the left direction or to the right direction by the turning operation of the left-right bending lever.

Japanese Patent Application Laid-Open Publication No. 2015-198790 discloses an endoscope in which the bending portion is bent to the up direction or to the down direction by turning the bending lever provided in the operation portion.

As described above, in the aforementioned Japanese Patent Application Laid-Open Publication No. 09-094218, Japanese Patent Application Laid-Open Publication No. 09-173279, and Japanese Patent Application Laid-Open Publication No. 2015-198790, the bending portion performs bending in a desired direction by a selective operation by an operator of the knob or the lever configured to be bent in two directions determined in advance. In other words, when the operator performs an operation of bending the bending portion in the up direction, for example, the bending portion is not bent to the left direction or to the right direction unless the left-right angle knob or the left-right bending lever is operated by mistake.

SUMMARY OF THE INVENTION

An endoscope according to an aspect of the present invention includes a bending portion bendable in all the directions including four directions: an up direction, a down direction, a left direction, and a right direction, one bending operation lever configured to bend the bending portion by being tilted, and a wire pulling mechanism provided integrally on the bending operation lever and including a lever tilting angle adjustment mechanism configured to set a first tilting angle at which the bending operation lever is tilted in order to bend the bending portion to at least one direction in the four directions by a predetermined bending angle and a second tilting angle at which the bending operation lever is tilted in order to bend the bending portion in a direction different from the at least one direction by a predetermined bending angle to different angles when the bending operation lever is tilted so as to bend the bending portion, in which the lever tilting angle adjustment mechanism includes an up pulling wire connection portion in which an up pulling wire having one end portion connected to the bending portion and configured to bend the bending portion to the up direction by pulling is disposed, a down pulling wire connection portion in which a down pulling wire having one end portion connected to the bending portion and configured to bend the bending portion to the down direction by pulling is disposed, a left pulling wire connection portion in which a left pulling wire having one end portion connected to the bending portion and configured to bend the bending portion to the left direction by pulling is disposed, and a right pulling wire connection portion in which a right pulling wire having one end portion connected to the bending portion and configured to bend the bending portion to the right direction by pulling is disposed, each of which swings correspondingly to a tilting operation of the bending operation lever, has a wire pulling member in which a center of the up pulling wire connection portion and a center of the down pulling wire connection portion are provided on an up-down direction tilting axis and a center of the left pulling wire connection portion and a center of the right pulling wire connection portion are provided on a left-right direction tilting axis, and an inter-center distance from a center of a fixing portion fixing the bending operation lever and the wire pulling member to the center of the up pulling wire connection portion and an inter-center distance to the center of the down pulling wire connection portion are different from an inter-center distance from the center of the fixing portion to the center of the left pulling wire connection portion and an inter-center distance to the center of the right pulling wire connection portion.

An endoscope according to an aspect of the present invention includes a bending portion bendable in all the directions including four directions: an up direction, a down direction, a left direction, and a right direction, one bending operation lever configured to bend the bending portion by being tilted, and a wire pulling mechanism provided integrally on the bending operation lever and including a lever tilting angle adjustment mechanism configured to set a first tilting angle at which the bending operation lever is tilted in order to bend the bending portion to at least one direction in the four directions by a predetermined bending angle and a second tilting angle at which the bending operation lever is tilted in order to bend the bending portion in a direction different from the at least one direction by the predetermined bending angle to different angles when the bending operation lever is tilted so as to bend the bending portion, in which the lever tilting angle adjustment mechanism has a wire pulling member including a first pulling wire connection portion in which a first pulling wire having one end portion connected to the bending portion is disposed, a second pulling wire connection portion in which a second pulling wire provided by facing the first pulling wire connection portion and sandwiching an up-down direction tilting axis and having one end portion connected to the bending portion is disposed, a third pulling wire connection portion in which a third pulling wire provided by facing the second pulling wire connection portion and sandwiching a left-right direction tilting axis and having one end portion connected to the bending portion is disposed, and a fourth pulling wire connection portion in which a fourth pulling wire provided by facing the third pulling wire connection portion and sandwiching the up-down direction tilting axis, provided by facing the first pulling wire connection portion and sandwiching the left-right direction tilting axis, and having one end portion connected to the bending portion is disposed, sets a first distance starting at a center of a fixing portion fixing the bending operation lever and the wire pulling member and ending at a first intersection between a straight line connecting a center of the first pulling wire connection portion and a center of the second pulling wire connection portion and the up-down direction tilting axis, a second distance starting at the center of the fixing portion and ending at a second intersection between a straight line connecting a center of the third pulling wire connection portion and a center of the fourth pulling wire connection portion and the up-down direction tilting axis, a third distance starting at the center of the fixing portion and ending at a third intersection between a straight line connecting the center of the second pulling wire connection portion and the center of the third pulling wire connection portion and the left-right direction tilting axis, and a fourth distance starting at the center of the fixing portion and ending at a fourth intersection between a straight line connecting the center of the fourth pulling wire connection portion and the center of the first pulling wire connection portion and the left-right direction tilting axis, and the first distance and the second distance are different from the third distance and the fourth distance.

An endoscope according to an aspect of the present invention includes a bending portion bendable in all the directions including four directions: an up direction, a down direction, a left direction, and a right direction, one bending operation lever configured to bend the bending portion by being tilted, and a wire pulling mechanism provided integrally on the bending operation lever and including a lever tilting angle adjustment mechanism configured to set a first tilting angle at which the bending operation lever is tilted in order to bend the bending portion to at least one direction in the four directions by a predetermined bending angle and a second tilting angle at which the bending operation lever is tilted in order to bend the bending portion in a direction different from the at least one direction by the predetermined bending angle to different angles when the bending operation lever is tilted so as to bend the bending portion, in which the lever tilting angle adjustment mechanism is a wire pulling amount enlargement mechanism provided in a middle portion of a wire and configured to enlarge/convert a pulling amount of the wire generated by a tilting operation of the bending operation lever with an enlargement rate determined in advance.

DETAILED DESCRIPTION OF THE PREFERRED EMBODIMENT(S)

Figure 1:
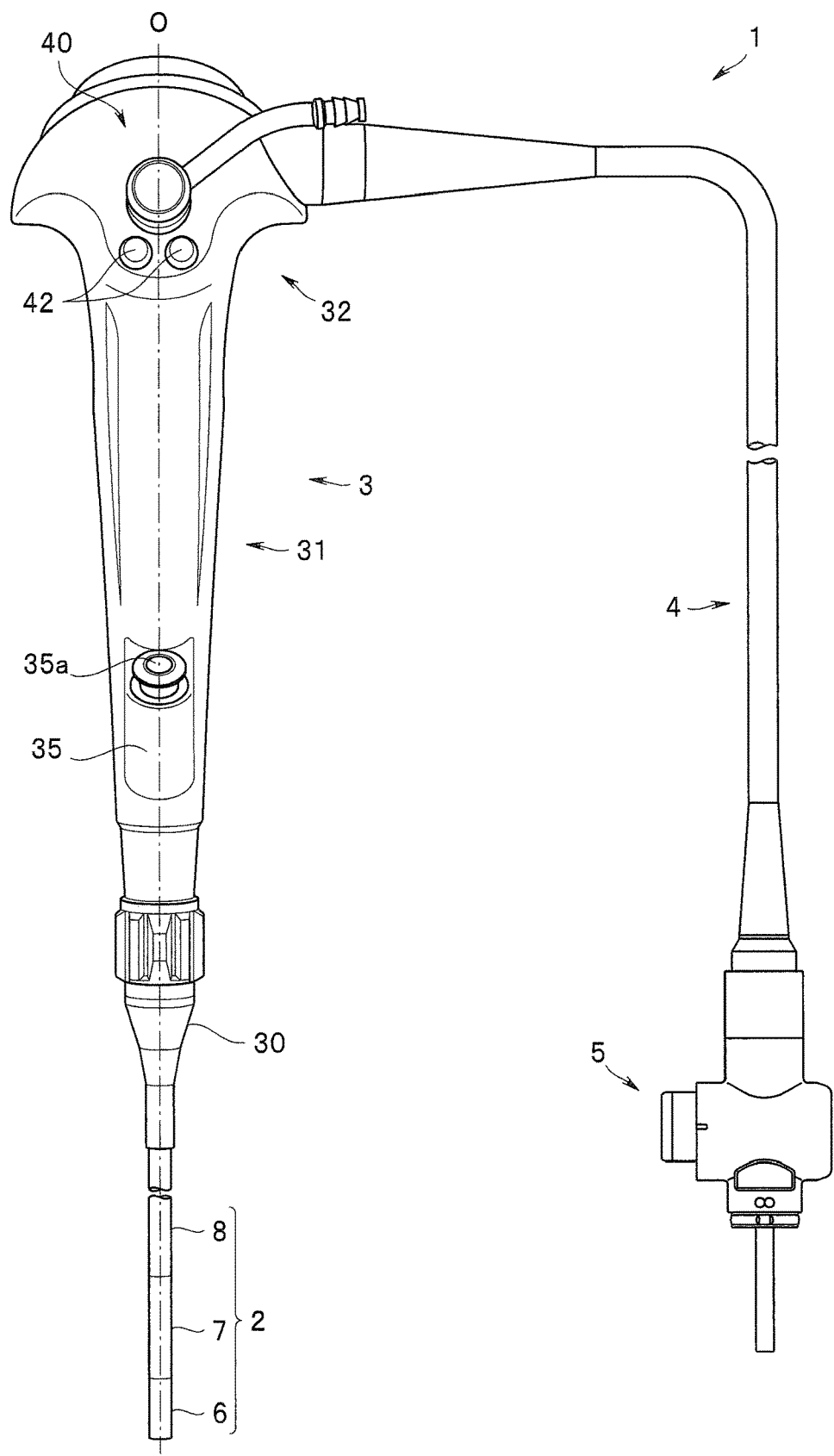
FIG. 1 is a front view illustrating an appearance of an endoscope.

Hereinafter, an embodiment of the present invention will be described by referring to the drawings.

Note that, in each of the drawings used for the following description, a scale is made different for each constituent element in some cases in order that each constituent element has such a size that can be recognized on the drawings. That is, the present invention is not limited to a quantity of the constituent elements, shapes of the constituent elements, a ratio of sizes of the constituent elements and a relative positional relationship of each constituent element described in the drawings.

Figure 2:
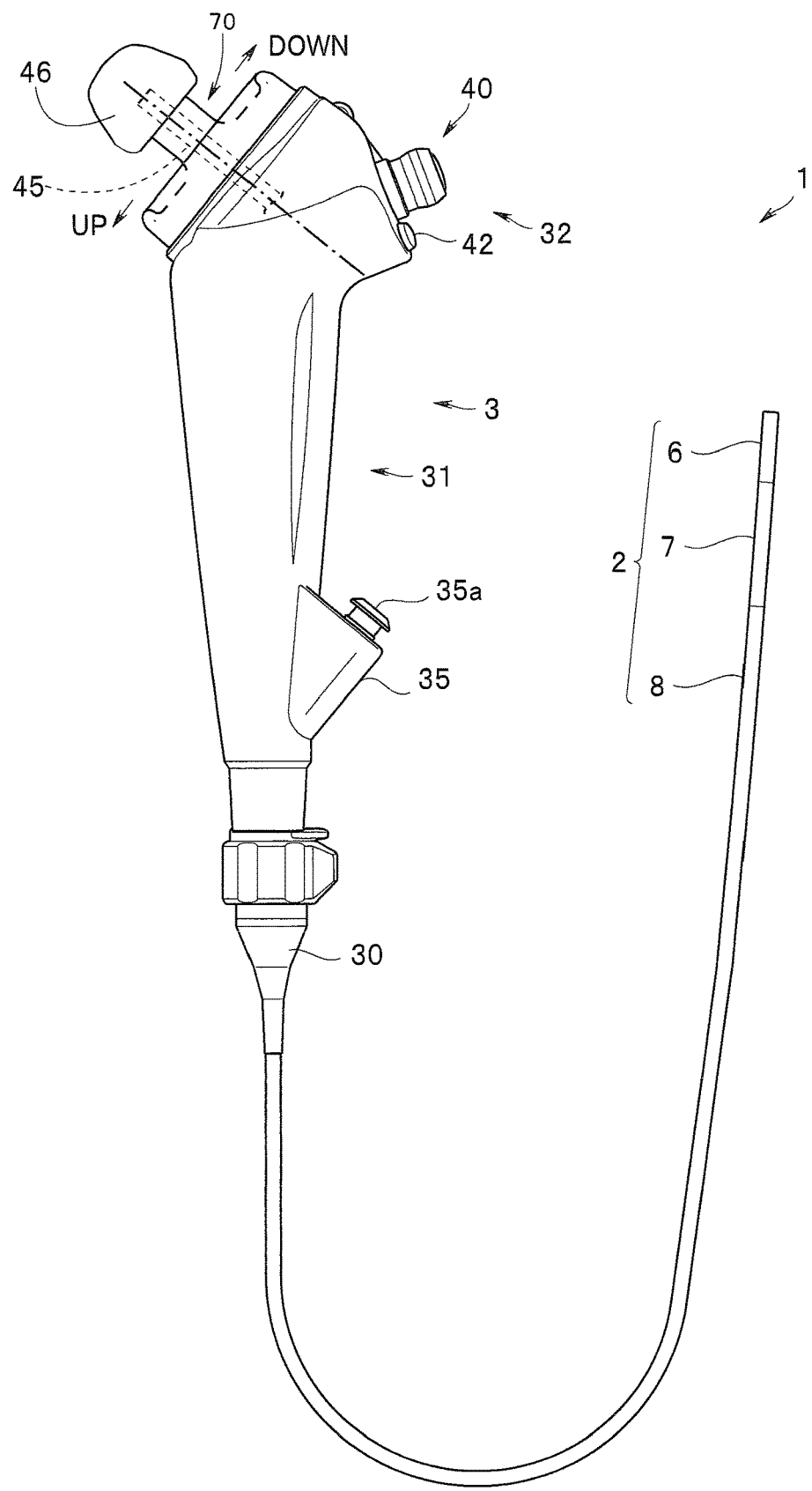
FIG. 2 is a right side view illustrating the appearance of the endoscope.
Figure 3:
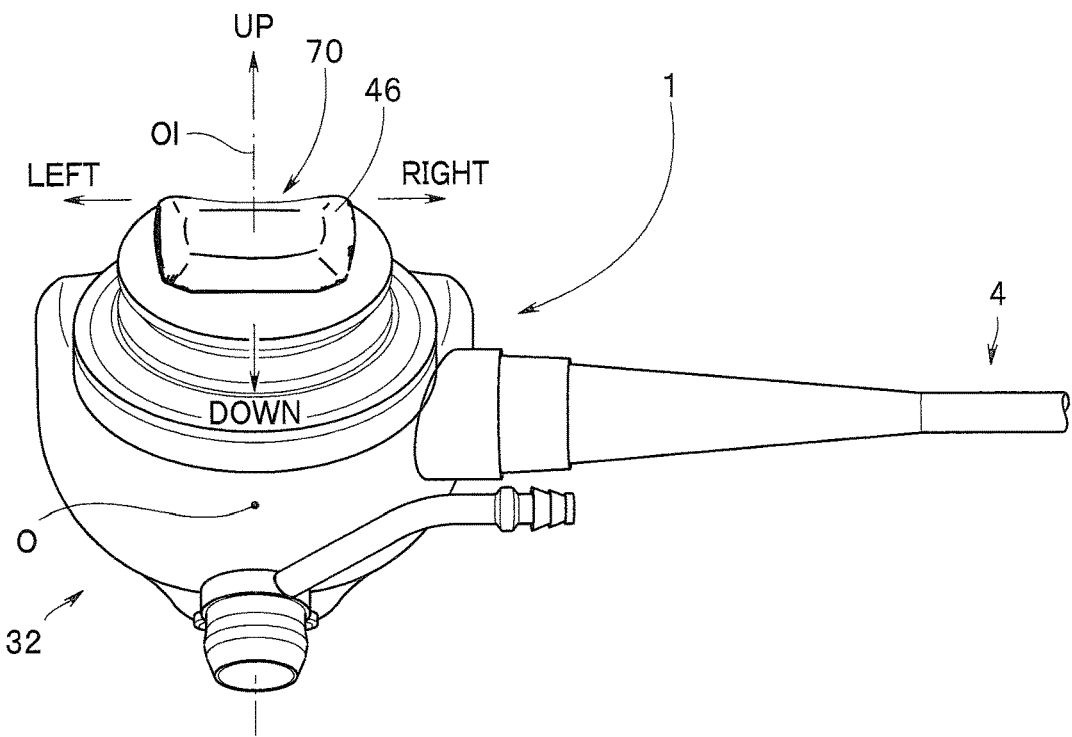
FIG. 3 is a top view illustrating the appearance of the endoscope.

An endoscope 1 as illustrated in FIGS. 1 to 3 includes an insertion portion 2 formed having an elongated shape, an operation portion 3 connected consecutively to a proximal end side of the insertion portion 2, and a universal cord 4 which is an endoscopic cable extended from the operation portion 3. An endoscopic connector 5 is disposed on an extended end portion of the universal cord 4.

The insertion portion 2 is a tubular member having flexibility and has a distal end portion 6, a bending portion 7, and a flexible tube portion 8 connected consecutively in order from a distal end side.

Figure 5:
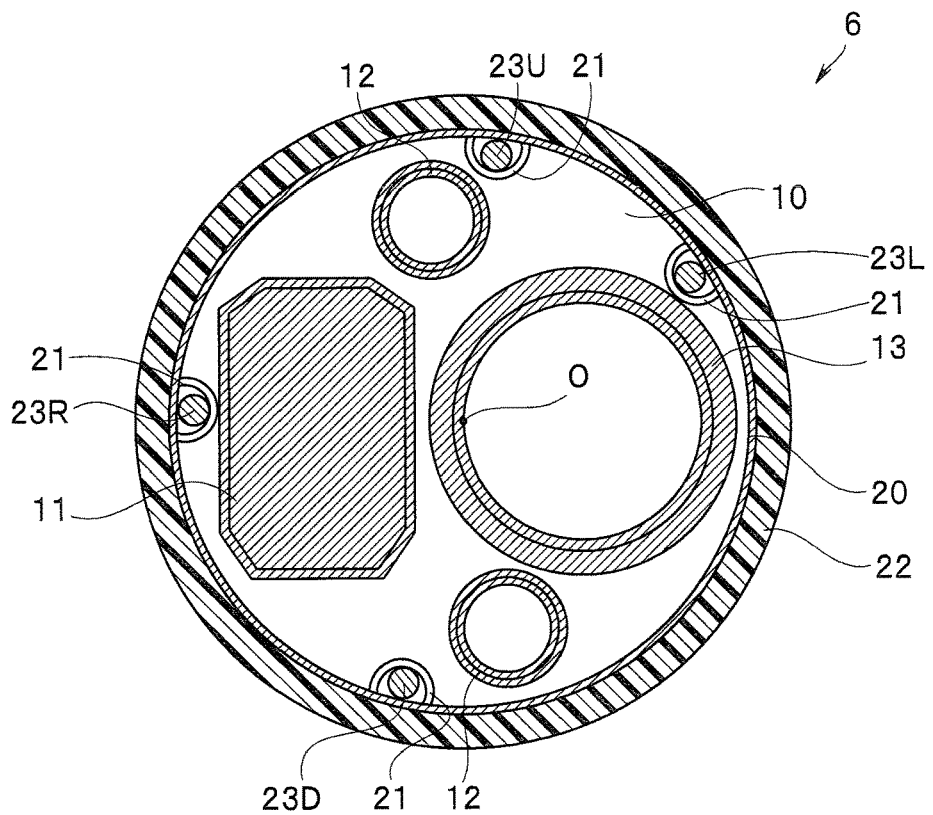
FIG. 5 is an Y5-Y5 line sectional view of FIG. 4.
Figure 4:
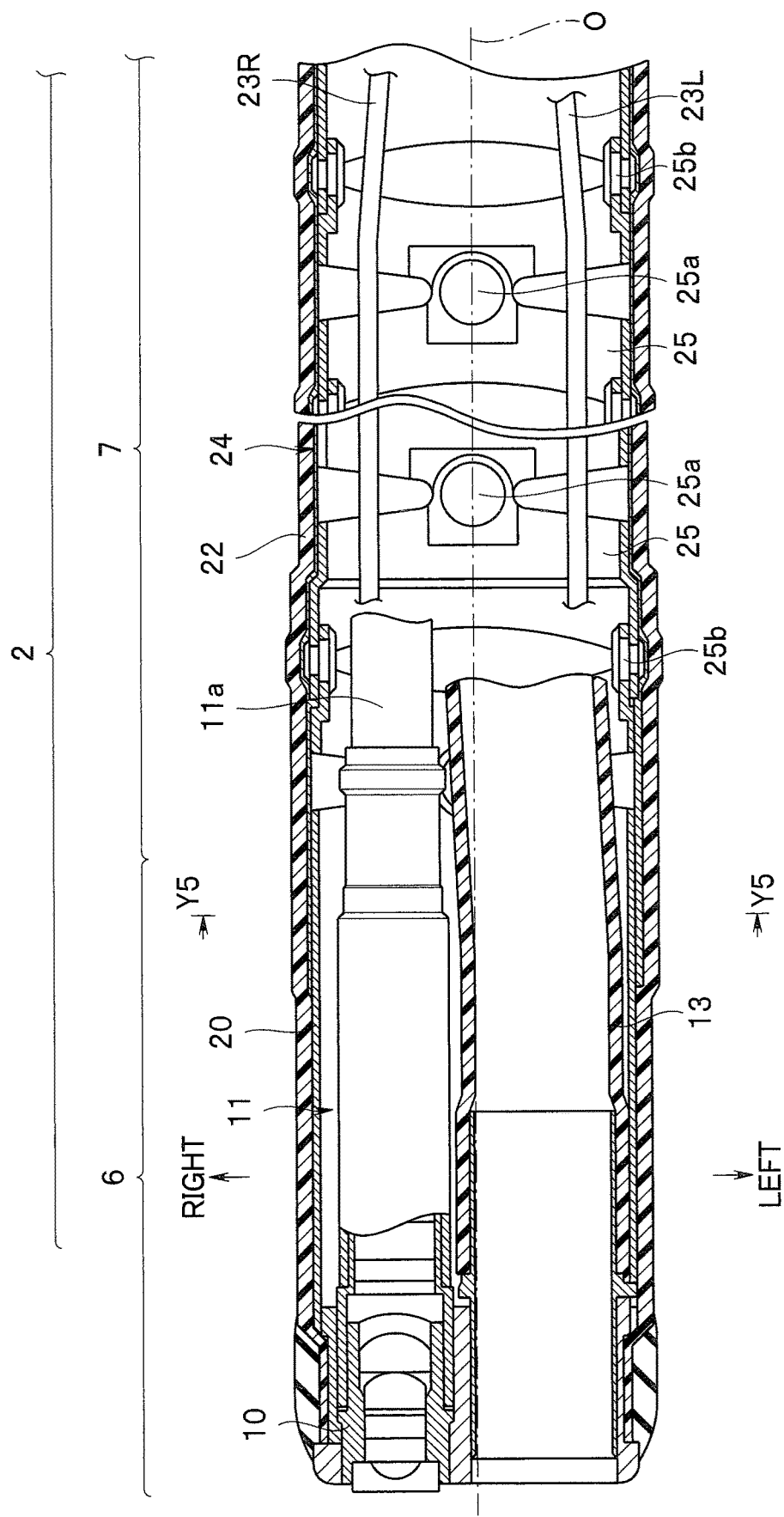
FIG. 4 is a view for explaining essential parts of a distal end portion and a bending portion.

As illustrated in FIGS. 4 and 5, a distal-end rigid portion 10 made of metal is provided in the distal end portion 6. An image pickup unit 11 incorporating an image pickup device such as a CCD and a CMOS, a pair of light guides 12 and a treatment instrument insertion channel 13, for example, are incorporated in the distal-end rigid portion 10.

A most distal bending piece 20 is externally fitted on the proximal end side of the distal-end rigid portion 10. Four wire fixing portions 21 are provided around an insertion axis O on an inner periphery of the most distal bending piece 20. A distal end portion of an up pulling wire 23U, a distal end portion of a down pulling wire 23D, a distal end portion of a left pulling wire 23L, and a distal end portion of a right pulling wire 23R corresponding to the up, down, left, and right directions, respectively, are fixed to each of the wire fixing portions 21. The pulling wires 23U, 23D, 23L, and 23R are extended into the operation portion 3 by passing through the insertion portion 2.

The bending portion 7 illustrated in FIG. 4 is configured to be capable of actively being bent in all the directions around the insertion axis O, including the up, down, left, and right directions in accordance with an operation input by an operator or the like to a bending operation device 70 which will be described later.

The bending portion 7 of the embodiment has a bending piece set 24 configured to be capable of bending by alternately connecting a bending piece 25 having a pivot portion 25a disposed in the up-down direction of the insertion portion 2 and a bending piece 25 having a pivot portion 25b disposed in the left-right direction of the insertion portion 2, for example. An outer periphery of the bending piece set 24 is covered by a bending rubber 22 extending from the distal end portion 6 side.

A signal cable 11a extended from the image pickup unit 11, light guides 12, and the treatment instrument insertion channel 13 are inserted inside the bending piece set 24 in arrangement similar to an inside of the distal end portion 6.

A wire guide (not shown) into which each of the pulling wires 23U, 23D, 23L, and 23R is inserted is provided in the predetermined bending piece 25 among those constituting the bending piece set 24.

The flexible tube portion 8 has flexibility passively bendable. The aforementioned signal cable 11a, the light guides 12, the treatment instrument insertion channel 13 and the like are inserted into the flexible tube portion 8 (none of them is shown, here).

The operation portion 3 is configured by mainly having a bend preventing portion 30, a grasping portion 31, and an operation portion body 32 as illustrated in FIGS. 1 and 2. The bend preventing portion 30 is connected to the flexible tube portion 8 in a state covering a proximal end of the flexible tube portion 8. The grasping portion 31 can be grasped by a hand of a user or the like and is connected to the flexible tube portion 8 through the bend preventing portion 30. The operation portion body 32 is connected consecutively to a proximal end side of the grasping portion 31.

Note that, in the embodiment, a direction around the insertion axis O and the like in the operation portion 3 are defined with the state where the user or the like grasps the grasping portion 31 as a reference. More specifically, front, rear, left, and right directions (a front surface, a rear surface, and left and right side surfaces and the like) are defined in the operation portion 3 with the user or the like grasping the grasping portion 31 as a reference.

The grasping portion 31 illustrated in FIG. 1 is formed having a shape symmetrical to the insertion axis O (center axis) capable of being grasped by the user or the like with either one of the left hand and the right hand.

The treatment instrument insertion portion 35 is provided on a front surface on the distal end side of the grasping portion 31. The treatment instrument insertion portion 35 includes a treatment instrument insertion port 35a into which various treatment instruments (not shown) are inserted. Inside the operation portion 3, the treatment instrument insertion port 35a and the treatment instrument insertion channel 13 are made to communicate through a branching member, not shown.

As illustrated in FIGS. 1 to 3, the operation portion body 32 is provided on the proximal end side of the grasping portion 31, and an operation button group 40 configured to execute various functions of the endoscope 1 is provided on a front surface side of the operation portion body 32.

On the other hand, on the rear surface side of the operation portion body 32, a bending operation lever 45 of the bending operation device 70 configured to perform the bending, operation to the bending portion 7 is disposed. The bending operation lever 45 is an axial body and has a finger contact portion 46 fixed to an end portion protruding outward of the operation portion.

Here, the operation portion body 32 and the bending operation device 70 will be described.

Figure 6:
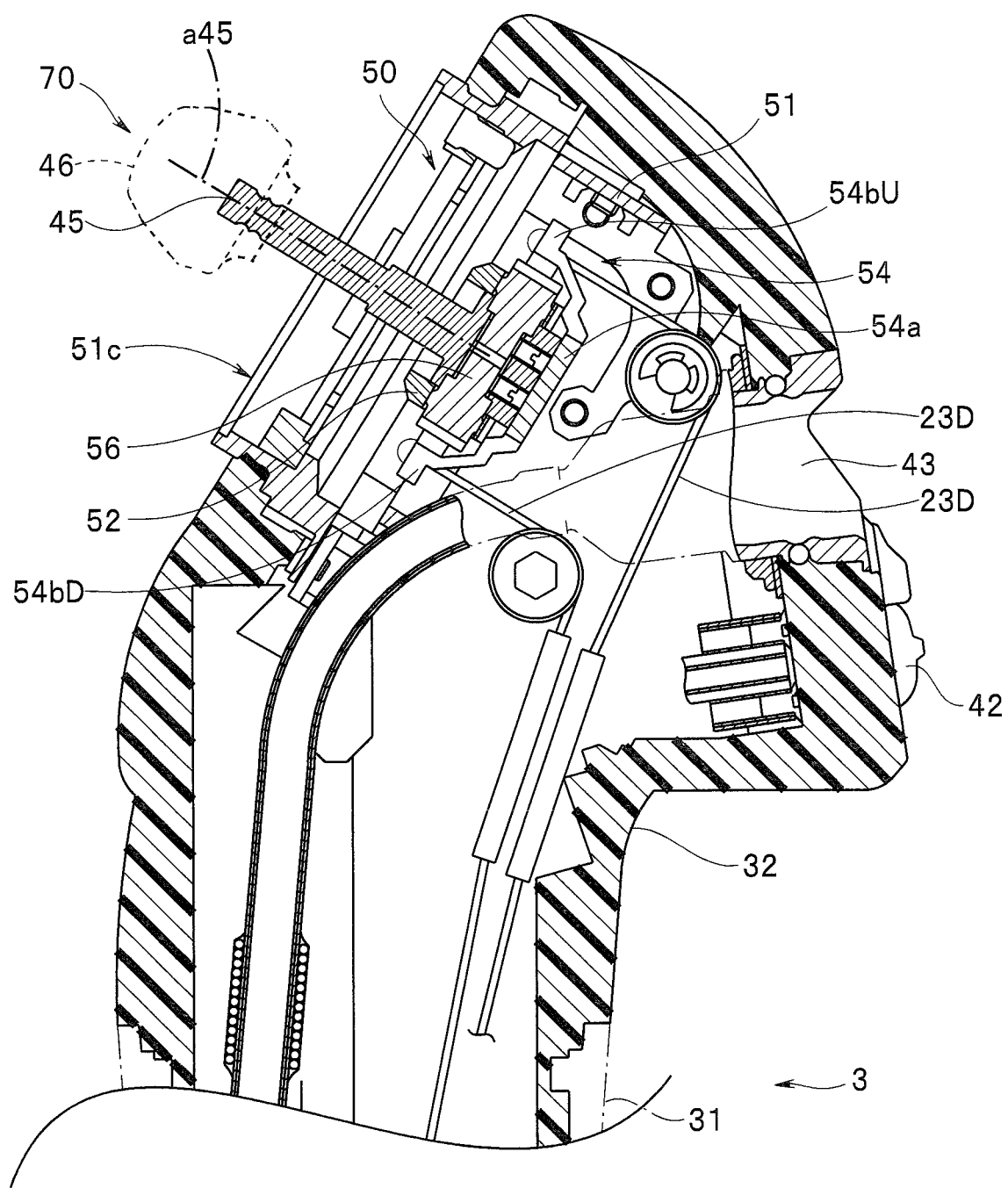
FIG. 6 is a view for explaining outline configuration of a bending operation device including a wire pulling mechanism including a bending operation lever and a lever tilting angle adjustment mechanism.

Reference numeral 45 illustrated in FIGS. 2 and 6 denotes the bending operation lever 45. The bending operation lever 45 is a joystick type lever configuring the bending operation device 70 and is capable of a tilting operation in all the directions including the four directions, that is, the up, down, left, and right directions. The finger contact portion 46 is provided on an end portion exposed to an outside of the bending operation lever 45. A thumb of the user or the like is disposed on the finger contact portion 46.

Figure 7A:
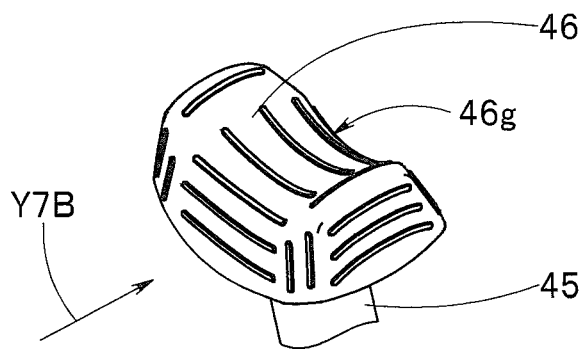
FIG. 7A is a perspective view of a finger contact portion.
Figure 7B:
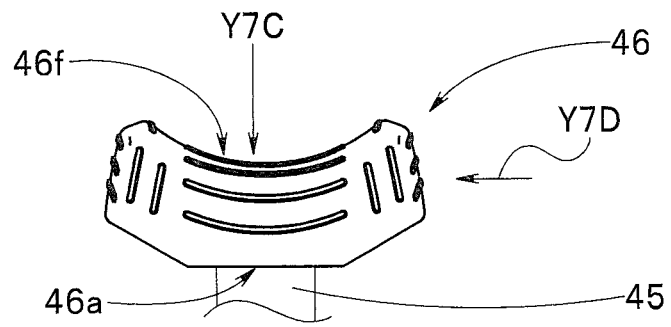
FIG. 7B is a view of the finger contact portion when seen from an arrow 7B side of FIG. 7A.
Figure 7C:
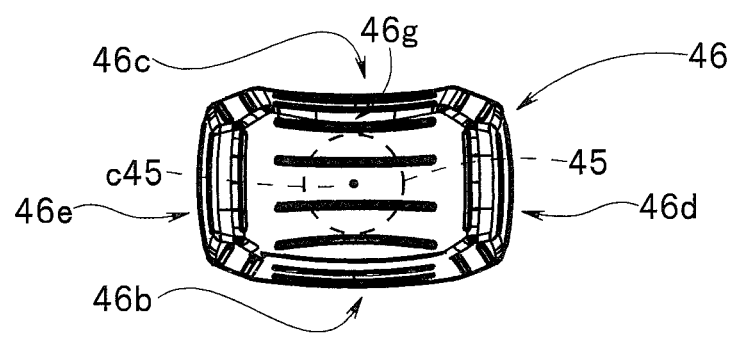
FIG. 7C is a view of the finger contact portion when seen from an arrow 7C side of FIG. 7B.
Figure 7D:
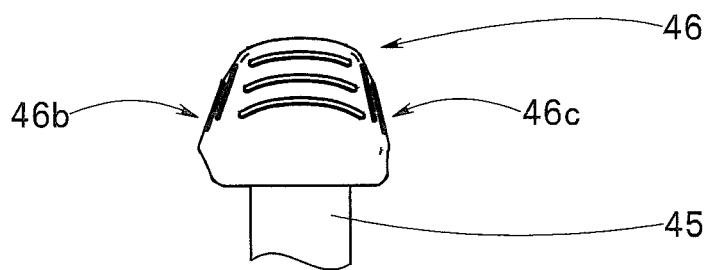
FIG. 7D is a view of the finger contact portion when seen from an arrow 7D side of FIG. 7B.

The finger contact portion 46 is a hexahedron illustrated in FIG. 7A, and a distal end portion of the bending operation lever 45 is mounted from a lower surface 46a side. As illustrated in FIGS. 7B, 7C, and 7D, the finger contact portion 46 has a surface on a side close to the grasping portion 31 as a projection-shaped surface 46b with a center protruding and a surface on a side separated from the grasping portion 31 as a recessed-shaped surface 46c with the center recessed. Moreover, an upper surface 46f is a recessed/curved surface with the center part recessed more than both edge ends.

As a result of such configuration, when the user disposes the thumb at a center part on the upper surface 46f of the finger contact portion 46, slip-out of the thumb from the finger contact portion 46 is prevented.

Moreover, by providing the recessed-shaped surface 46c and the upper surface 46f of the recessed/curved surface on the finger contact portion 46, the center part of a finger contact edge portion 46g provided along a ridge line between the upper surface 46f and the recessed-shaped surface 46c is shifted to a center c45 side of the bending operation lever 45 mounted on the finger contact portion 46. Thus, when the user performs a pulling operation for tilting the bending operation lever 45 to the grasping portion 31 side which is an UP direction illustrated in FIGS. 2 and 3 and the like, for example, from a state where the user disposes the thumb on the upper surface 46f, the user can smoothly perform the pulling operation by disposing the thumb on the finger contact edge portion 46g with a slight shift to the recessed-shaped surface 46c side without moving the thumb from the upper surface 46f to the recessed-shaped surface 46c.

On the other hand, the center part of the projection-shaped surface 46b is located at a position separated from a center of the bending operation lever 45 mounted on the finger contact portion 46 by providing the projection-shaped surface 46b on the finger contact portion 46. Thus, when a user performs a pushing operation for tilting the bending operation lever 45 to a direction so as to be separated from the grasping portion 31 which is a DOWN direction illustrated in FIGS. 2 and 3 and the like, for example, from a state where the user disposes the thumb on the upper surface 46f, the user can perform the pushing operation with a smaller moving amount of the thumb by disposing the thumb on the center part side of the projection-shaped surface 46b.

Note that the pulling operation is assumed to be in the UP direction and the pushing operation in the DOWN direction in the above, but the pushing operation may be in the UP direction and the pulling direction may be in the DOWN direction.

As illustrated in FIG. 3, the bending operation lever 45 is disposed at a symmetric position on a rear surface side which is a surface opposite to a front surface side on which a suction button 41a of the operation portion body 32 is disposed. A center axis a45 of the bending operation lever 45 illustrated in FIG. 6 is provided upright to an outer side end surface 51c of a housing 51 on the operation portion body 32 by being positioned on the insertion axis O.

Then, when the bending operation lever 45 is in an upright state, the bending portion 7 is in a straight state, and the bending portion 7 is configured to bend as the bending operation lever 45 is tilted.

As illustrated in FIGS. 2 and 3, with regard to the tilting direction of the bending operation lever 45, a left-right width direction of the operation portion 3 which is a direction orthogonal to the insertion axis O is defined as the left-right direction of the tilting operation, and a direction orthogonal to the left-right width direction is defined as the up-down direction of the tilting operation.

More specifically, a left side on the drawing of FIG. 3 is a left tilting direction for bending the bending portion 7 to the left side, a right side on the drawing is a right tilting direction for bending the bending portion 7 to the right side, a lower side on the drawing is an up tilting direction for bending the bending portion 7 to the upper side, and an upper side on the drawing is a down tilting direction for bending the bending portion 7 to the lower side.

As illustrated in FIG. 6, a wire pulling mechanism 50 configuring the bending operation device 70 is provided consecutively to the end portion of the bending operation lever 45 located in the operation portion 3. An end portion of each of the pulling wires 23U, 23D, 23L, and 23R is connected to a wire pulling member 54 which will be described later of the wire pulling mechanism 50, respectively, as will be described later.

Here, details of the wire pulling mechanism 50 will be described.

Figure 8:
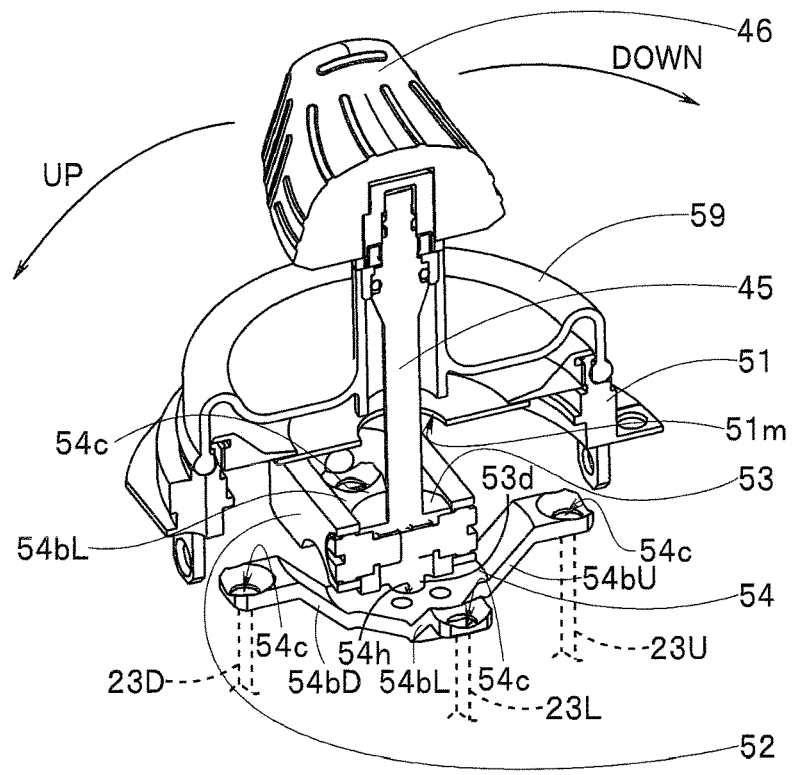
FIG. 8 is a view for explaining configuration of a bending operation device.
Figure 9:
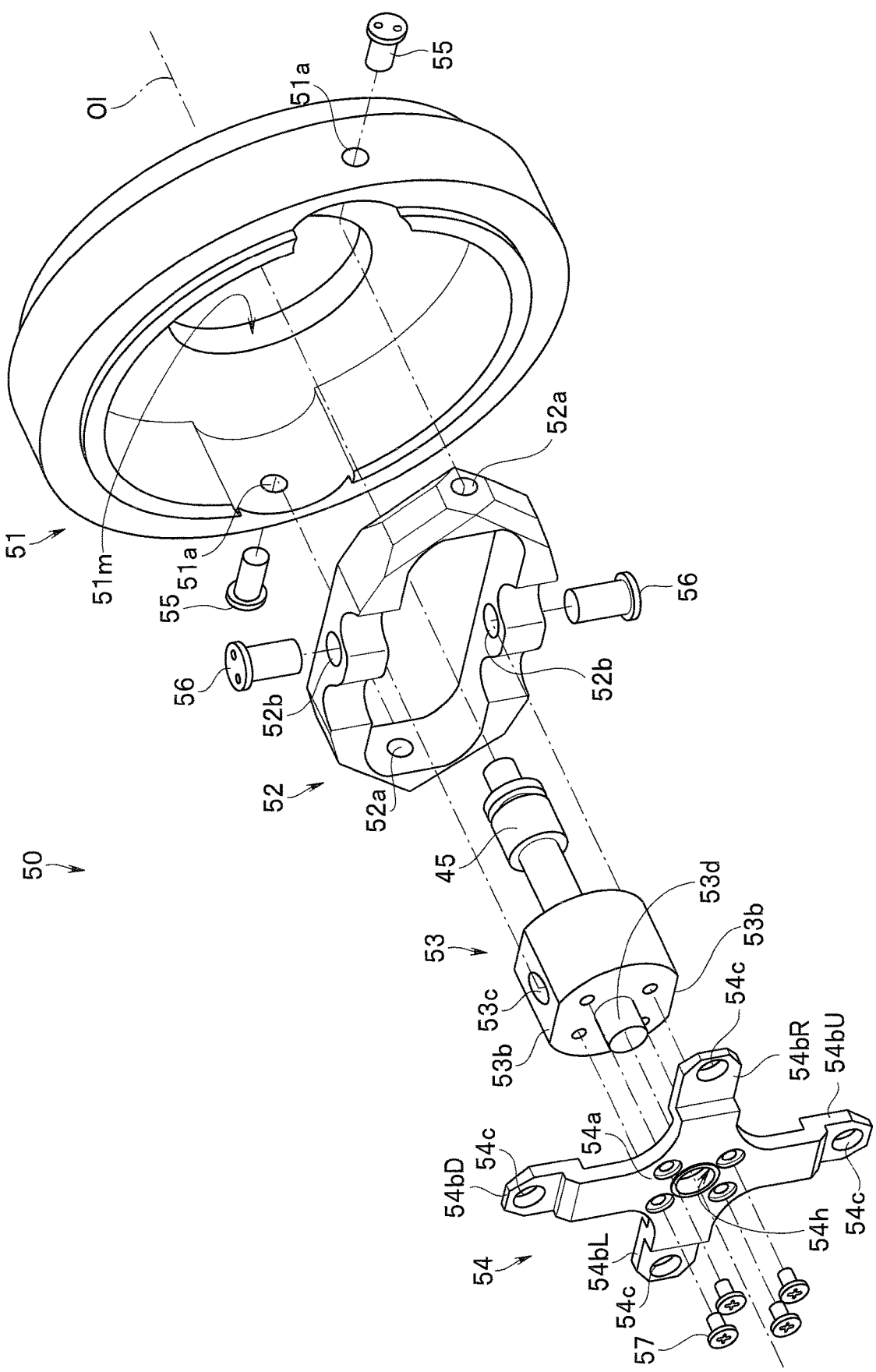
FIG. 9 is an exploded perspective view for explaining the configuration of the bending operation device.

As illustrated in FIGS. 6, 8, and 9, the wire pulling mechanism 50 is configured by having the housing 51, a turnable frame 52, a base member 53, and the wire pulling member 54.

The housing 51 is a cylindrical member fixed to the operation portion body 32 and has an opening 51m which is a through hole in which the bending operation lever 45 is disposed to be capable of tilting. The housing 51 has a shaft hole 51a faced with a peripheral wall of the housing 51 drilled.

A bending boot 59 is mounted on an outer side of the housing 51. The bending boot 59 is a cover member formed of a cylindrical elastic member, holds the bending operation lever 45 in the upright state to be capable of a tilting operation, and seals the opening 51m.

The turnable frame 52 is a frame body having a substantially rectangular shape, for example, and is pivotally supported turnably (swingably) in the housing 51. A pair of bottomed holes 52a faced with each other is drilled at a center of both end portions in a longitudinal direction of the turnable frame 52.

Then, a support pin 55 inserted into each of the shaft holes 51a of the housing 51, respectively, is locked in each of the bottomed holes 52a, whereby the turnable frame 52 is pivotally supported turnably with respect to the housing 51.

Moreover, a pair of shaft holes 52b faced with each other is drilled at the center of both end portions in a short side direction of the turnable frame 52.

The base member 53 has a substantially columnar shape and is pivotally supported in the turnable frame 52, turnably (swingably). In the embodiment, the bending operation lever 45 is integrally formed on a center axis of the base member 53.

A pair of flat portions 53b faced with each other is formed on a periphery part of the base member 53. A through hole 53c is drilled having an opening in the flat portions 53b. A support pin 56 disposed in each of the shaft holes 52b of the turnable frame 52 is locked in the through hole 53c. As a result, the base member 53 is pivotally supported turnably with respect to the turnable frame 52.

As described above, since the base member 53 is supported by the housing 51 through the turnable frame 52, the bending operation lever 45 integral with the base member 53 is capable of tilting in an arbitrary direction. Reference numeral 53d is a base projection portion and is a rod-shaped projection protruding from a center of a base end surface 53e.

Note that the bending operation lever 45 may be a separate member from the base member 53. In this case, the bending operation lever 45 is integrated with/fixed to the base member 53 by a fastening member or an adhesive.

The wire pulling member 54 is fixed to the base member 53. The wire pulling member 54 is a plate-shaped member extending arm portions 54b to four directions different from each other, for example, and has a cross shape in which an angle formed by the arm portions 54b adjacent to each other is set to 90 degrees as illustrated in FIGS. 10A to 10E.

Wire disposing holes 54c are formed as pulling wire connection portions corresponding to the up, down, left, and right pulling wires 23U, 23D, 23L, and 23R on an end portion side of each of the arm portions 54b, respectively. A wire mounting member (not shown) fixed to the end portion of each of the pulling wires 23U, 23D, 23L, and 23R is disposed on the wire disposing hole 54c. That is, each of the arm portions 54b is an up-wire arm portion 54bU, a down-wire arm portion 54bD, a left-wire arm portion 54bL, and a right-wire arm portion 54bR, respectively. A center of the wire disposing hole 54c of the up-wire arm portion 54bU and the center of the wire disposing hole 54c of the down-wire arm portion 54bD are provided on an up-down direction titling axis Lud, and the center of the wire disposing hole 54c of the left-wire arm portion 54bL and the center of the wire disposing hole 54c of the right-wire arm portion 54bR are provided on a left-right direction tilting axis Llr.

A fixed hole 54h which is a through hole and in which a base projection portion 53d is fitted is formed at a center portion 54a of the cross-shaped wire pulling member 54.

Note that the wire pulling member 54 is not limited to the cross shape as long as the angle formed by adjacent straight lines connecting the center of the fixed hole 54h and the center of each of the wire disposing holes 54c is 90 degrees and may have a circular shape, a square shape or the like.

The arm portion 54b is the lever tilting angle adjustment mechanism, and lengths of the four arm portions 54b are set as appropriate.

Figure 10A:
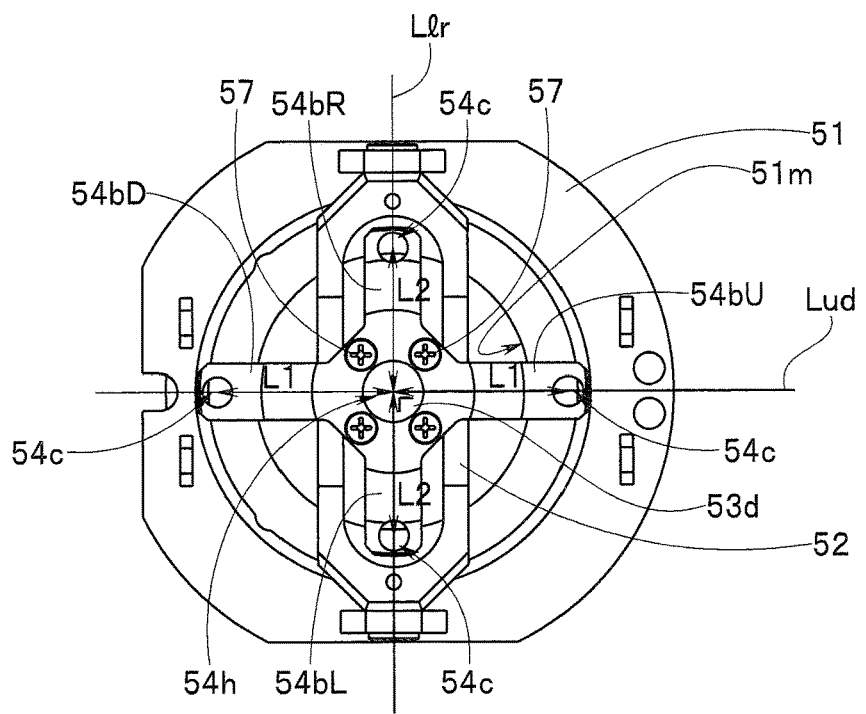
FIG. 10A is a view for explaining a configuration example of the lever tilting angle adjustment mechanism.

More specifically, with regard to the up-wire arm portion 54bU and the down-wire arm portion 54bD in FIG. 10A, a distance from the center of the fixed hole 54h which is the center of the fixed portion to the center of the wire disposing hole 54c is set to a first inter-center distance L1. On the other hand, with regard to the left-wire arm portion 54bL and the right-wire arm portion 54bR, the distance from the center of the fixed hole 54h to the center of the wire disposing hole 54c is set to a second inter-center distance L2.

Then, the first inter-center distance L1 is set longer than the second inter-center distance L2.

In the embodiment, the wire pulling member 54 is integrated with/fixed to the base member 53 by a screw 57, for example, in a state where the base projection portion 53d is fitted in the fixed hole 54h. As a result, the bending operation lever 45 is integrated with/fixed to the wire pulling member 54 through the base member 53.

Thus, when the bending operation lever 45 is tilted, a distal end side of each of the arm portions 54b is made to swing and displaced in conjunction with the tilting operation.

Here, a case where the bending operation lever 45 is tilted at an angle θ to the up direction and a case where it is tilted at the angle θ to the left direction are compared.

Figure 11:
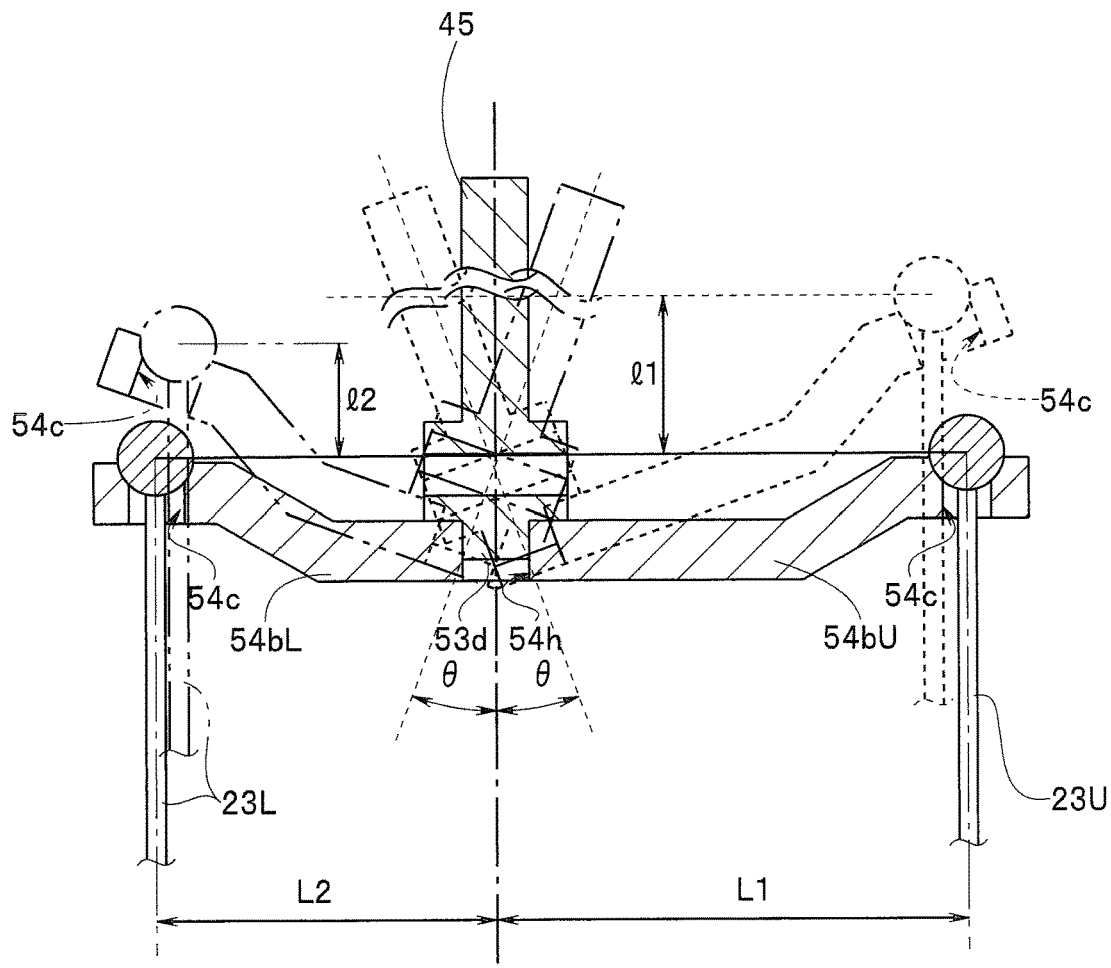
FIG. 11 is a view for explaining an action of the lever tilting angle adjustment mechanism.

The bending operation lever 45 is tilted at the angle θ. Then, as illustrated on the right side of a center line in FIG. 11, the up-wire arm portion 54bU is made to swing as indicated by a broken line, and the end portion of the up pulling wire 23U is moved by a first moving distance l1. On the other hand, the left-wire arm portion 54bL is made to swing as indicated by a two-dot chain line as illustrated on the left side of the center line in FIG. 11, and the end portion of the left pulling wire 23L is moved by a second moving distance l2.

As described above, since the first inter-center distance L1 and the second inter-center distance L2 are different in a relationship determined in advance, the first moving distance l1 and the second moving distance l2 are different in the case of tilting at the same angle θ, and the first moving distance l1 becomes larger than the second moving distance l2. That is, a pulling amount of the up pulling wire 23U becomes larger than the pulling amount of the left pulling wire 23L.

The above means that, in the configuration of the embodiment, when the bending operation lever 45 is tilted to the up direction and the left direction at the same angle θ, for example, a bending angle to the up direction and a bending angle to the left direction of the bending portion 7 are made different, and the up-direction bending angle becomes larger than the left-direction bending angle.

In other words, a ratio of the bending angle of the bending portion 7 to the first tilting angle of the bending operation lever 45 when the bending portion 7 is to be bent in the up-down direction is made larger than a ratio of the bending angle of the bending portion 7 to the second tilting angle of the bending operation lever 45 when the bending portion 7 is to be bent in the left-right direction.

That is, in the bending operation lever 45, response sensitivity to the up-down bending is set higher than the response sensitivity to the left-right bending. Thus, when the bending portion 7 is to be bent in the up-down direction at the bending angle determined in advance, the bending operation lever 45 is tilted in the up-down direction at the first tilting angle, while when the bending portion 7 is to be bent in the left-right direction at the same bending angle, the bending operation lever 45 needs to be tilted in the left-right direction at the second tilting angle larger than the first tilting angle. Therefore, the bending portion 7 starts bending by slightly tilting the bending operation lever 45 in the up-down direction, while the bending in the left-right direction is not started unless the bending operation lever 45 is tilted largely in the up-down direction.

As described above, the first inter-center distance L1 and the second inter-center distance L2 are set to different lengths and then, the first inter-center distance L1 is made longer than the second inter-center distance L2 so that the response sensitivity when the bending operation lever 45 is bent in the up-down direction is made higher than the response sensitivity when the bending operation lever 45 is bent in the left-right direction.

According to the configuration, when the user grasps the grasping portion 31 of the operation portion 3, disposes the thumb of the grasping hand on the finger contact portion 46 and tilts the bending operation lever 45 so as to bend the bending portion 7 to the up direction or the down direction, if the thumb is slightly moved to the left direction or the right direction, and the bending operation lever 45 is tilted to the left direction or the right direction, an angle at which the bending portion 7 is bent to the left direction or the right direction is small. Therefore, the bending portion 7 is bent to one direction of the up direction and the down direction mainly in response to the tilting operation to the up direction or the down direction of the bending operation lever 45.

In the aforementioned embodiment, the direction where the response sensitivity is higher is determined to be the up direction and the down direction in advance. However, the direction where the response sensitivity is higher is not limited to the two directions, that is, the up direction and the down direction, and two directions, that is, the left direction and the right direction, for example, may be made the directions with high response sensitivity.

Figure 10B:
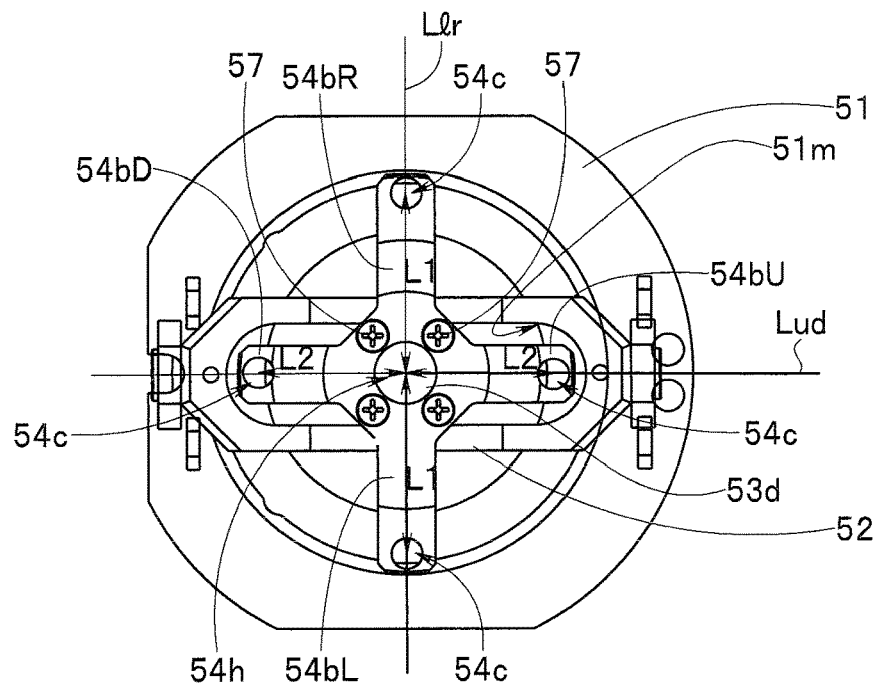
FIG. 10B is a view for explaining another configuration example of the lever tilting angle adjustment mechanism.

In this case, a distance from the center of the fixed hole 54$h$ of the left-wire arm portion 54$b$L to the center of the wire disposing hole 54$c$ and a distance from the center of the fixed hole 54$h$ of the right-wire arm portion 54$b$R to the center of the wire disposing hole 54$c$ are set to the first inter-center distance L1 as illustrated in FIG. 10B. On the other hand, the distance from the center of the fixed hole 54$h$ of the up-wire arm portion 54$b$U to the center of the wire disposing hole 54$c$ and the distance from the center of the fixed hole 54$h$ of the down-wire arm portion 54$b$D to the center of the wire disposing hole 54$c$ are set to the second inter-center distance L2. As a result, the response sensitivity of the bending operation lever 45 to left bending and right bending becomes higher than the response sensitivity to up bending and down bending. Therefore, the bending portion 7 is bent to one direction, that is, the left direction or the right direction mainly in response to the tilting operation of the bending operation lever 45 in the left direction or the right direction.

In the above, the direction where the response sensitivity is higher is two directions, that is, up and down, or left and right. However, the direction where the response sensitivity is higher may be one direction, that is, only the up direction, for example.

Figure 10C:
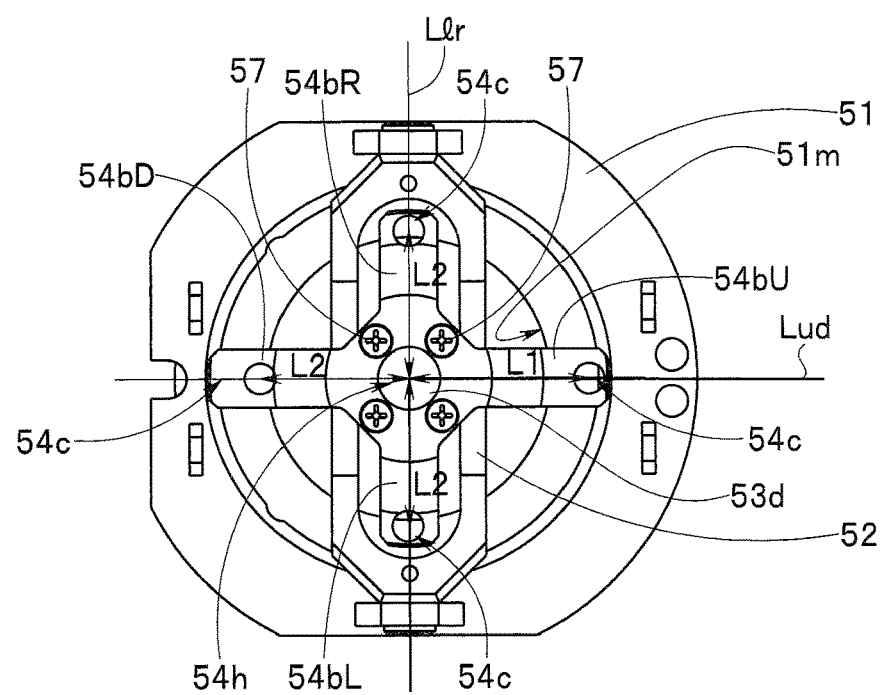
FIG. 10C is a view for explaining a different configuration example of the lever tilting angle adjustment mechanism.

In this case, the distance from the center of the fixed hole 54$h$ of the up-wire arm portion 54$b$U to the center of the wire disposing hole 54$c$ is set to the first inter-center distance L1 as illustrated in FIG. 10C. On the other hand, the distances from the center of the fixed hole 54$h$ of the down-wire arm portion 54$b$D to the center of the wire disposing hole 54$c$, from the center of the fixed hole 54$h$ of the left-wire arm portion 54$b$L to the center of the wire disposing hole 54$c$, and from the center of the fixed hole 54$h$ of the right-wire arm portion 54$b$L to the center of the wire disposing hole 54$c$ are set to the second inter-center distance L2. As a result, the response sensitivity to the up bending of the bending operation lever 45 becomes higher than the response sensitivity to the down bending, the left bending, and the right bending and thus, the bending portion 7 is bent to the up direction mainly in response to the tilting operation of the bending operation lever 45 to the up direction.

Figure 10D:
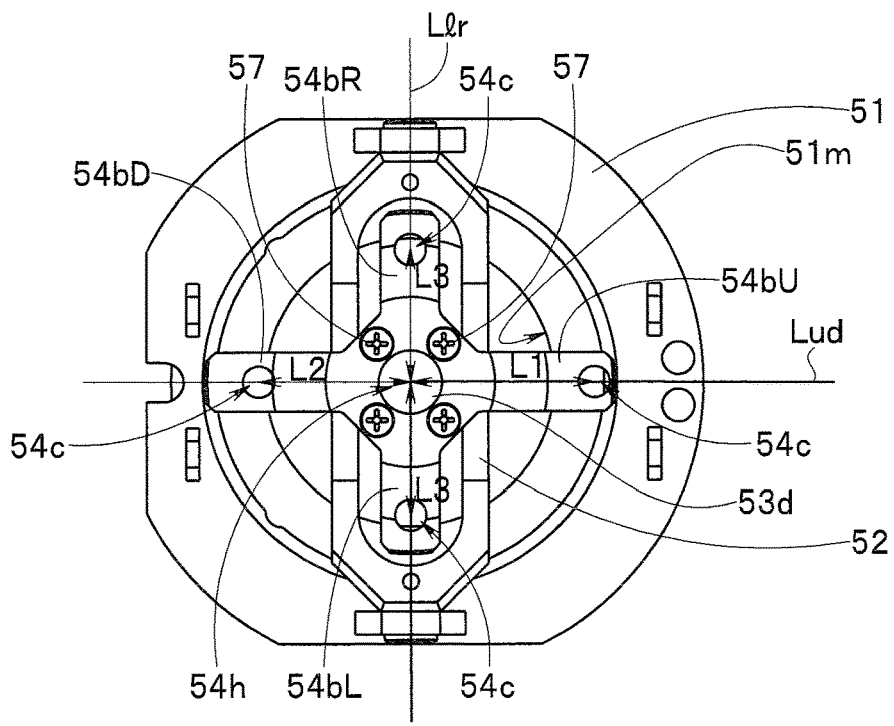
FIG. 10D is a view for explaining still another configuration example of the lever tilting angle adjustment mechanism.

In the aforementioned embodiment, the distance from the center of the fixed hole 54$h$ of the up-wire arm portion 54$b$U to the center of the wire disposing hole 54$c$ is set to the first inter-center distance L1, and the distance from the center of the fixed hole 54$h$ other than the up direction to the center of the wire disposing hole 54$c$ is set to the second inter-center distance L2. However, the distance from the center of the fixed hole 54$h$ of the up-wire arm portion 54$b$U to the center of the wire disposing hole 54$c$ may be set to the first inter-center distance L1, the distance from the center of the fixed hole 54$h$ of the down-wire arm portion 54$b$D to the center of the wire disposing hole 54$c$ may be set to the second inter-center distance L2, and a distance from the center of the fixed hole 54$h$ of the left-wire arm portion 54$b$L to the center of the wire disposing hole 54$c$ and a distance from the center of the fixed hole 54$h$ of the right-wire arm portion 54$b$L to the center of the wire disposing hole 54$c$ may be set to a third inter-center distance L3 shorter than the second inter-center distance L2 as illustrated in FIG. 10D, for example.

As a result, in the bending operation lever 45, the response sensitivity to the up bending becomes higher than the response sensitivity to the down bending, and the response sensitivity to the down bending becomes higher than the response sensitivity to the left bending and the right bending. That is, the bending portion 7 is set by having three steps of response sensitivity of the tilting operations in the up direction, the down direction, and the left/right directions of the bending operation lever 45 in order and is bent to the up direction with the most favorable response.

Figure 10E:
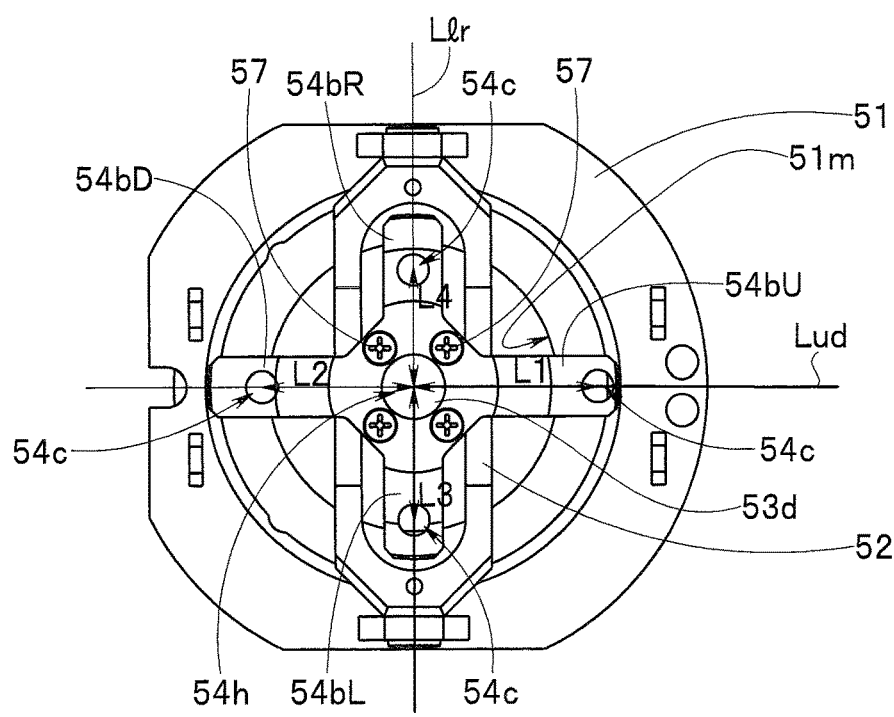
FIG. 10E is a view for explaining a still different configuration example of the lever tilting angle adjustment mechanism.

Note that the distance from the center of the fixed hole 54$h$ of the up-wire arm portion 54$b$U to the center of the wire disposing hole 54$c$ may be set to the first inter-center distance L1, the distance from the center of the fixed hole 54$h$ of the down-wire arm portion 54$b$D to the center of the wire disposing hole 54$c$ may be set to the second inter-center distance L2, a distance from the center of the fixed hole 54$h$ of the left-wire arm portion 54$b$L to the center of the wire disposing hole 54$c$ may be set to a third inter-center distance L3, and a distance from the center of the fixed hole 54$h$ of the right-wire arm portion 54$b$L to the center of the wire disposing hole 54$c$ may be set to a fourth inter-center distance L4 shorter than the third inter-center distance L3 as illustrated in FIG. 10E, for example.

As a result, in the bending operation lever 45, the response sensitivity to the up bending becomes higher than the response sensitivity to the down bending, the response sensitivity to the down bending becomes higher than the response sensitivity to the left bending, and the response sensitivity to the left bending becomes higher than the response sensitivity to the right bending. That is, the bending portion 7 is set by having four steps of response sensitivity of the tilting operations in the up direction, the down direction, the left direction, and the right direction of the bending operation lever 45 in order and is bent to the up direction with the most favorable response.

Moreover, the aforementioned one direction is not limited to the up direction, and the one direction may be the down direction, the left direction or the right direction. That is, the order of the response sensitivity in three steps is not limited to the aforementioned up direction, the down direction, and the left/right directions of the bending operation lever 45, but various settings can be made such as the three steps of the up direction, the left direction, the down/right directions, the three steps of the up direction, the right direction, and the down/left directions, and the three steps of the down direction, the up direction, and the left/right directions.

Moreover, in the above, the two directions are a combination of the up direction and the down direction and a combination of the left direction and the right direction. However, the combination of the two directions may be a combination of the up direction and the left direction, a combination of the up direction and the right direction, a combination of the down direction and the left direction or a combination of the down direction and the right direction.

In the embodiment, the combination of the bending angle and the response sensitivity can be set freely depending on a type of the endoscope. If the up-direction bending angle, the down-direction bending angle, the left-direction bending angle, and the right-direction bending angle of the bending portion 7 in the endoscope 1 are made same, for example, a movable range of the bending operation lever only needs to be set small in a direction with high response sensitivity, while the movable range of the bending operation lever only needs to be set large in a direction with low response sensitivity. If the response sensitivity in the up-down direction is set high and the response sensitivity in the left-right direction is set low, for example, in order to set the bending angle in all the directions, that is, the up, the down, the left, and the right directions to 180 degrees, for example, the movable range of the bending operation lever 45 is set small in the up-down direction and wide in the left-right direction. As a result, the bending angles in all the directions, that is, the up, the down, the left, and the right directions can be set same while the bending operation function for allowing bending easily only in a desired direction is provided.

Moreover, if the bending angle in at least one direction in the up-direction bending angle, the down-direction bending angle, the left-direction bending angle, and the right-direction bending angle of the bending portion 7 in the endoscope 1 is made different from the bending angle in another direction, the bending angle in the direction with high response sensitivity only needs to be set large, and the bending angle in the direction with low response sensitivity only needs to be set small. If the response sensitivity in the up-down direction is to be set high and the response sensitivity in the left-right direction is to be set low, for example, the bending angle in the up-down direction is set to 270 degrees, for example, and the bending angle in the left-right direction is set to 180 degrees, for example. As a result, the tilting operation with the movable ranges of the bending operation lever 45 substantially the same in the up-down direction and the left-right direction can be realized.

The aforementioned lever tilting angle adjustment mechanism is not limited to the configuration in which the inter-center distances from the centers of the fixed holes 54h provided in the four wire arm portions 54b to the centers of the wire disposing holes 54c are set to different distances but may be a wire pulling amount enlargement mechanism provided in the middle of the pulling wires 23U and 23D and a relay wire 68.

Figure 12:
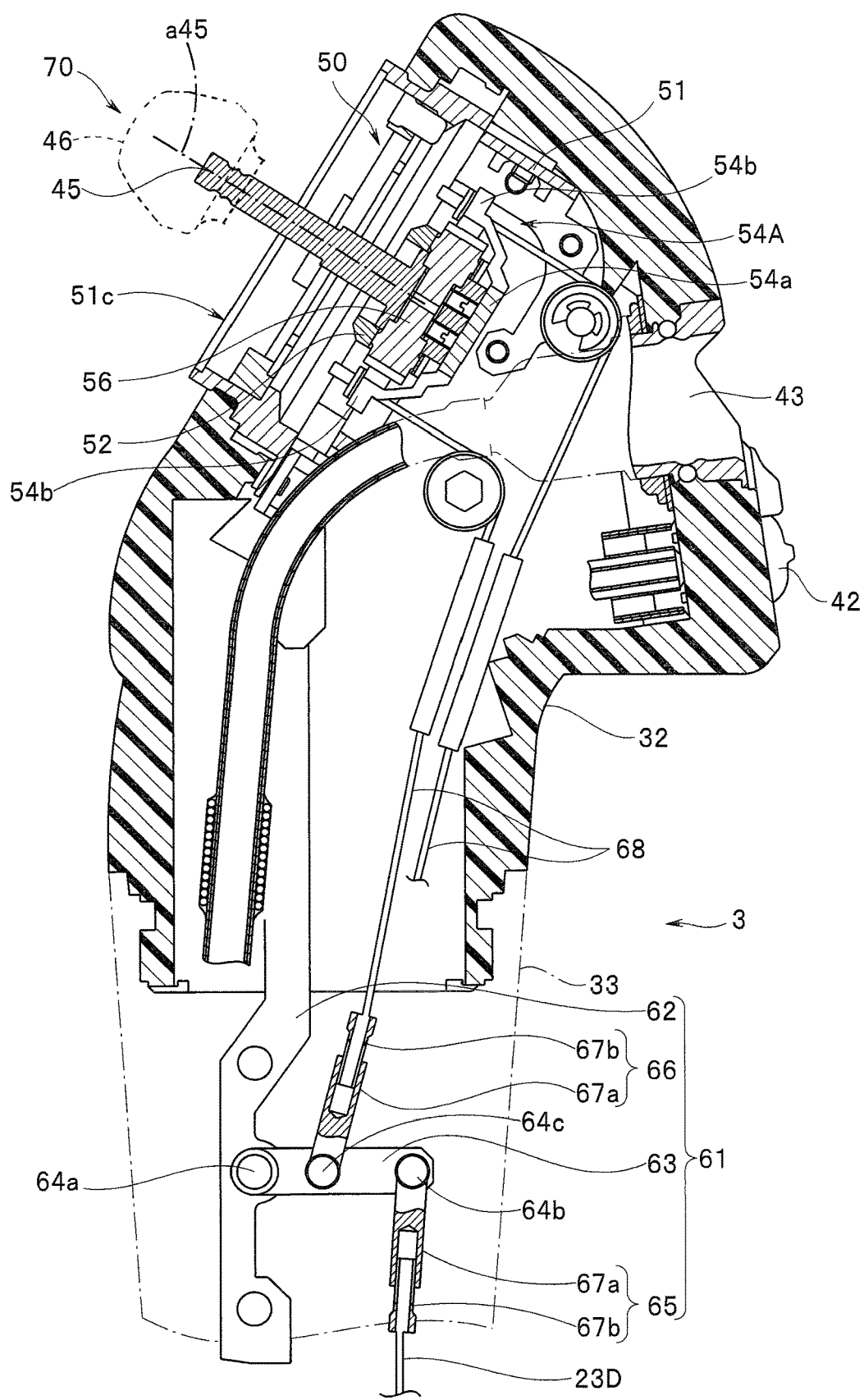
FIG. 12 is a view for explaining the wire pulling mechanism including an enlargement link mechanism as a wire pulling amount enlarging mechanism.

In the wire pulling mechanism 50 illustrated in FIG. 12, a wire pulling member 54A is a plate-shaped member extending the arm portions 54b in the four directions different from each other similarly to the above, for example, and has a cross shape in which the angle formed by the arm portions 54b adjacent to each other is set to 90 degrees.

The wire disposing hole 54c is formed on the end portion side of each of the arm portions 54b of the wire pulling member 54A of the embodiment, respectively. In the embodiment, the inter-center distance from the center of the fixed hole 54h in each of the arm portions 54b to the center of the wire disposing hole 54c is set to the same distance.

And in the embodiment, one end portion of the relay wire 68 is disposed on two arm portions in the four arm portions 54b, that is, on the wire disposing hole 54c of the up-wire arm portion and the wire disposing hole 54c of the down-wire arm portion.

Note that the end portion of the left pulling wire 23L is disposed in the wire disposing hole 54c of the left-wire arm portion and the end portion of the right pulling wire 23R is disposed in the wire disposing hole 54c of the right-wire arm portion 54b, which are the remaining two arm portions. The other configuration is similar to the aforementioned embodiment, and the same reference numerals are given to the same members, and description will be omitted.

The other end portions of the two relay wires 68 are extended toward an enlargement link mechanism 61 which is also referred to herein as the wire pulling amount enlargement mechanism.

The enlargement link mechanisms 61 are prepared in two for up bending and down bending. An up-bending enlargement link mechanism 61U and a down-bending enlargement link mechanism 61D have the same configuration and thus, the configuration of the down-bending enlargement link mechanism 61D will be described, and the description of the up-bending enlargement link mechanism 61U will be omitted.

The down-bending enlargement link mechanism 61 includes a base plate 62 integrally fixed to the operation portion 3, a first link member 63, a first wire connecting member 65 which is a second link member, and a second wire connecting member 66 which is a third link member.

The first wire connecting member 65 and the second wire connecting member 66 have the same structure and have a connecting portion body 67a on which a female screw portion is provided on one end portion side and a wire connecting portion 67b on which a male screw portion is provided on one end portion side.

The first link member 63 has one end portion turnably connected to the base plate 62 with a first turnable pin 64a as a fulcrum. The other end portion of the connecting portion body 67a of the first wire connecting member 65 is turnably connected to a free end side which is the other end portion of the first link member 63 with a second turnable pin 64b as an action point. The other end portion of the connecting portion body 67a of the second wire connecting member 66 is turnably connected to a position determined in advance of a middle portion between the one end portion and the other end portion of the first link member 63 with a third turnable pin 64c as a power point.

A proximal end portion of the down pulling wire 23D is fixed to the other end portion of the wire connecting portion 67b of the first wire connecting member 65, and the other end portion of the relay wire 68 is fixed to the other end portion of the wire connecting portion 67b of the second wire connecting member 66.

The down pulling wire 23D and the relay wire 68 are connected by screwing the male screw portion of the wire connecting portion 67b with the female screw portion of the connecting portion body 67a. A screw state between the connected down pulling wire 23D and the relay wire 68 is adjusted as appropriate so as to have a length determined in advance.

In the embodiment, when the operator tilts the bending operation lever 45 in the left direction or in the right direction, for example, the left-wire arm portion 54b or the right-wire arm portion 54b is made to swing, and the end portion of the left pulling wire 23L or the end portion of the right pulling wire 23R is moved by a predetermined distance. As a result, the left pulling wire 23L or the right pulling wire 23R is moved, and the bending portion 7 is bent in the right direction or in the left direction.

On the other hand, if the operator tilts the bending operation lever 45 in the up direction or in the down direction, for example (here, a case of the tilting operation in the down direction will be described by referring to the drawings), the down-wire arm portion 54b is made to swing, and the end portion of the relay wire 58 is moved by a predetermined distance. Since the relay wire 58 is connected to the first link member 63 through the second connecting member 66, the first link member 63 is rotated so as to fall to the wire pulling mechanism 50 side around the first turnable pin 64a with movement of the relay wire 58.

Then, the down pulling wire 23D is connected to the other end portion of the first link member 63 through the first connecting member 65. Thus, the down pulling wire 23D is moved, and the bending portion 7 is bent to the down direction with the rotational movement of the first link member 63.

Here, since the second connecting member 65 is connected to the middle portion of the first link member 63, and the first connecting member 65 is connected at a position most separated from the first turnable pin 64a which is the other end portion of the first link member 63, the moving amount of the down pulling wire 23D becomes larger than the moving amount of the relay wire 58.

The above means that, if the bending operation lever 45 is tilted to the up direction and the left direction by the same angle θ similarly to the aforementioned embodiment, for example, since the wire pulling amount enlargement mechanism 61 is provided, the pulling amount of the up pulling wire 23U is enlarged/converted at an enlargement rate determined in advance from the pulling amount of the left pulling wire 23L, and the bending angle of the bending portion 7 to the up direction becomes larger than the left direction bending angle.

In other words, the ratio of the bending angle of the bending portion 7 to the tilting angle of the bending operation lever 45 when the bending portion 7 is to be bent in the up-down direction is made larger than the ratio of the bending angle of the bending portion 7 to the tilting angle of the bending operation lever 45 when the bending portion 7 is bent to the left-right direction so that the response sensitivity when the bending operation lever 45 is bent in the up-down direction is made higher than the response sensitivity when being bent in the left-right direction.

According to the configuration, when the user grasps the grasping portion 31 of the operation portion 3, disposes the thumb of the grasping hand on the finger contact portion 46, and tilts the bending operation lever 45 so as to bend the bending portion 7 to the up direction or to the down direction, if the thumb is slightly moved to the left direction or to the right direction, and the bending operation lever 45 is tilted to the left direction or to the right direction, the angle at which the bending portion 7 is bent to the left direction or to the right direction is small. Therefore, the bending portion 7 is bent to one direction, that is, to the up direction or to the down direction mainly in response to the tilting operation of the bending operation lever 45 to the up direction or to the down direction.

Note that the moving amount of the up pulling wire 23U and the moving amount of the down pulling wire 23D to the moving amount of the relay wire 58 can be adjusted as appropriate by separating the action point from the fulcrum farther than the power point and then, by setting the distance from the fulcrum to the power point and the distance from the fulcrum to the action point as appropriate.

Moreover, in the aforementioned embodiment, the wire pulling amount enlargement mechanism 61 is provided between the up pulling wire 23U and the relay wire 68 and between the down pulling wire 23D and the relay wire 68. However, the wire pulling amount enlargement mechanism 61 may be provided in two directions, that is, in the left direction and the right direction.

In this case, the wire pulling amount enlargement mechanism 61 is provided between the left pulling wire 23L and the relay wire 68 and between the right pulling wire 23R and the relay wire 68. As a result, the bending portion 7 is bent to one direction, that is, to the left direction or to the right direction mainly in response to the tilting operation of the bending operation lever 45 to the left direction or to the right direction.

In the above, the wire pulling amount enlargement mechanism 61 is provided in the two directions of the up direction and the down direction and in the two directions of the left direction and the right direction. However, the wire pulling amount enlargement mechanism 61 may be provided in two directions, that is, the up direction and the left direction, provided in two directions, that is, the up direction and the right direction, provided in two directions, that is, the down direction and the left direction or provided in two directions, that is, the down direction and the right direction.

Moreover, instead of providing the wire pulling amount enlargement mechanism 61 in two directions, the wire pulling amount enlargement mechanism 61 may be provided only in one direction, that is, in the up direction, for example.

In this case, the wire pulling amount enlargement mechanism 61 is provided only between the up pulling wire 23U and the relay wire 68. As a result, the bending portion 7 is bent to one direction, that is, the up direction, mainly in response to the tilting operation of the bending operation lever 45 to the up direction.

Here, the aforementioned one direction is not limited to the up direction but the one direction may be any one of the down direction, the left direction or the right direction.

Moreover, in addition to provision between the up pulling wire 23U and the relay wire 68 and between the down pulling wire 23D and the relay wire 68, the wire pulling amount enlargement mechanism 61 may be provided between the left pulling wire 23L and the relay wire 68 and between the right pulling wire 23R and the relay wire 68. That is, four units of the wire pulling amount enlargement mechanisms 61 may be provided.

In this case, the enlargement link mechanisms 61 and 61A with different enlargement rates are prepared as the four wire pulling amount enlargement mechanisms 61, for example. The enlargement link mechanism 61 illustrated in FIG. 12 has a first enlargement rate and hereinafter shall be described as the first enlargement link mechanism 61. The enlargement link mechanism 61A illustrated in FIG. 13 has a second enlargement rate and hereinafter shall be described as the second enlargement link mechanism 61A.

Figure 13:
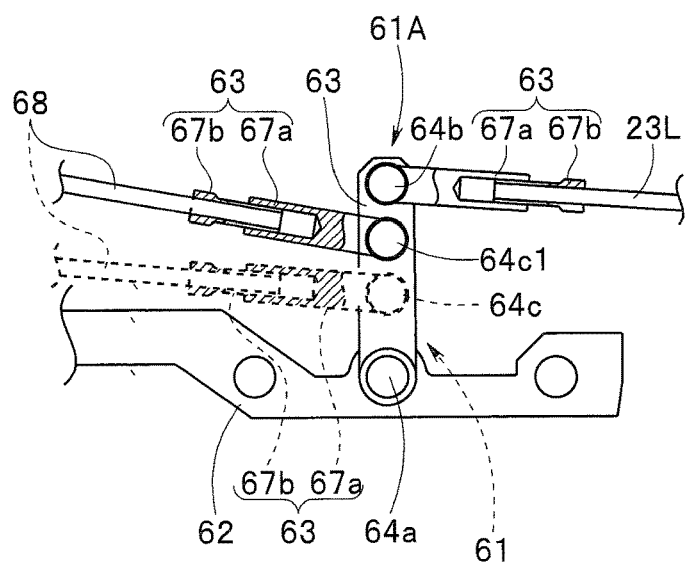
FIG. 13 is a view for explaining one configuration example of the enlargement link mechanism with a different enlargement rate.

As illustrated in FIG. 13, the distance from the fulcrum to the power point is different between the first enlargement link mechanism 61 and the second enlargement link mechanism 61A. More specifically, in the second enlargement link mechanism 61A, a position of a third turnable pin 64c1 is disposed closer to a second turnable pin 64b side which is an action point than the position of a third turnable pin 64c of the first enlargement link mechanism 61, for example.

As a result, a distance from the first turnable pin 64a which is a fulcrum of the second enlargement link mechanism 61A to the third turnable pin 64c1 which is the power point is larger than the distance from the first turnable pin 64a of the first enlargement link mechanism 61 to the third turnable pin 64c. Thus, the first enlargement rate of the first enlargement link mechanism 61 indicated by a broken line is larger than the second enlargement rate of the second enlargement link mechanism 61A indicated by a solid line.

Then, the first enlargement link mechanism 61 is provided between the up pulling wire 23U and the relay wire 68 and between the down pulling wire 23D and the relay wire 68, and the second enlargement link mechanism 61A is provided between the left pulling wire 23L and the relay wire 68 and between the right pulling wire 23R and the relay wire 68.

As a result, a ratio of the bending angle of the bending portion 7 to the tilting angle of the bending operation lever 45 when the bending portion 7 is bent to the up-down direction becomes larger than the ratio of the bending angle of the bending portion 7 to the tilting angle of the bending operation lever 45 when the bending portion 7 is bent to the left-right direction. That is, the response sensitivity when the bending operation lever 45 is bent in the up-down direction becomes higher than the response sensitivity when the bending operation lever 45 is bent in the left-right direction.

According to the configuration, when the user is to tilt the bending operation lever 45 so as to bend the bending portion 7 to the up direction or to the down direction, if the thumb is slightly moved to the left direction or to the right direction, and the bending operation lever 45 is tilted to the left direction or to the right direction, the angle at which the bending portion 7 is bent to the left direction or to the right direction is small. Therefore, the bending portion 7 is bent to one direction, that is, to the up direction or to the down direction mainly in response to the tilting operation of the bending operation lever 45 to the up direction or to the down direction.

Note that, to the contrary to the above, the first enlargement link mechanism 61 may be provided between the left pulling wire 23L and the relay wire 68 and between the right pulling wire 23R and the relay wire 68, and the second enlargement link mechanism 61A may be provided between the up pulling wire 23U and the relay wire 68 and between the down pulling wire 23D and the relay wire 68. As a result, the bending portion 7 is bent to one direction, that is, to the left direction or to the right direction mainly in response to the tilting operation of the bending operation lever 45 to the left direction or to the right direction.

Moreover, the first enlargement link mechanism 61 may be provided between the up pulling wire 23U and the relay wire 68 and between the left pulling wire 23L and the relay wire 68, and the second enlargement link mechanism 61A may be provided between the down pulling wire 23D and the relay wire 68 and between the right pulling wire 23R and the relay wire 68. As a result, the bending portion 7 is bent to one direction, that is, to the up direction or to the left direction mainly in response to the tilting operation of the bending operation lever 45 to the up direction or to the left direction.

The first enlargement link mechanism 61 may be provided between the up pulling wire 23U and the relay wire 68 and between the right pulling wire 23R and the relay wire 68, and the second enlargement link mechanism 61A may be provided between the down pulling wire 23D and the relay wire 68 and between the left pulling wire 23L and the relay wire 68. As a result, the bending portion 7 is bent to one direction, that is, to the up direction or to the right direction mainly in response to the tilting operation of the bending operation lever 45 to the up direction or to the right direction.

The first enlargement link mechanism 61 may be provided between the down pulling wire 23D and the relay wire 68 and between the left pulling wire 23L and the relay wire 68, and the second enlargement link mechanism 61A may be provided between the up pulling wire 23U and the relay wire 68 and between the right pulling wire 23R and the relay wire 68. As a result, the bending portion 7 is bent to one direction, that is, to the down direction or to the left direction mainly in response to the tilting operation of the bending operation lever 45 to the down direction or to the left direction.

The first enlargement link mechanism 61 may be provided between the down pulling wire 23D and the relay wire 68 and between the right pulling wire 23R and the relay wire 68, and the second enlargement link mechanism 61A may be provided between the up pulling wire 23U and the relay wire 68 and between the left pulling wire 23L and the relay wire 68. As a result, the bending portion 7 is bent to one direction, that is, to the down direction or to the right direction mainly in response to the tilting operation of the bending operation lever 45 to the down direction or to the right direction.

Note that, in the above, the two first enlargement link mechanisms 61 and the two second enlargement link mechanisms 61A are provided in two directions each in the four directions. However, the first enlargement link mechanism 61 may be provided in one direction or only between the up pulling wire 23U and the relay wire 68, for example, and the second enlargement link mechanism 61A may be provided in the remaining three directions, excluding the up direction, that is, between the down pulling wire 23D and the relay wire 68, between the left pulling wire 23L and the relay wire 68, and between the right pulling wire 23R and the relay wire 68.

As a result, the bending portion 7 is bent to one direction of the up direction mainly in response to the tilting operation of the bending operation lever 45 to the up direction.

Here, the aforementioned one direction is not limited to the up direction but the one direction may be the down direction, the left direction or the right direction.

In the aforementioned embodiment, the first enlargement link mechanism 61 or the second enlargement link mechanism 61A is provided between the pulling wire 23 in any one of the directions and the relay wire 68. However, in addition to the first enlargement link mechanism 61 and the second enlargement link mechanism 61A, a third enlargement link mechanism 61B illustrated in FIG. 14A, and a fourth enlargement link mechanism 61C illustrated in FIG. 14B may be provided between the pulling wire 23 in any one of the directions and the relay wire 68.

Figure 14A:
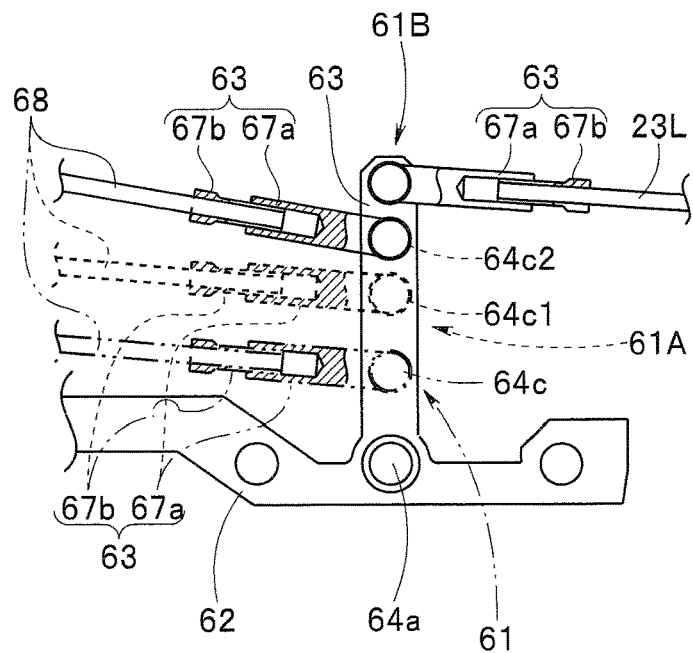
FIG. 14A is a view for explaining another configuration example of the enlargement link mechanism with a different enlargement rate.

The distance from the fulcrum to the power point is different among the third enlargement link mechanism 61B, the first enlargement link mechanism 61, and the second enlargement link mechanism 61A illustrated in FIG. 14A. More specifically, a position of a third turnable pin 64c2 in the third enlargement link mechanism 61B is disposed closer to the second turnable pin 64b side which is an action point than the position of the third turnable pin 64c1 of the second enlargement link mechanism 61A.

As a result, the distance from the first turnable pin 64a which is the fulcrum of the third enlargement link mechanism 61B to the third turnable pin 64c2 which is the power point is larger than the distance from the first turnable pin 64a of the second enlargement link mechanism 61A to the third turnable pin 64c1. Thus, a third enlargement rate of the third enlargement link mechanism 61B indicated by a solid line is further smaller than the second enlargement rate of the second enlargement link mechanism 61A indicated by a broken line.

Then, the first enlargement link mechanism 61 is provided between the up pulling wire 23U and the relay wire 68, the second enlargement link mechanism 61A is provided between the down pulling wire 23D and the relay wire 68, and the third enlargement link mechanism 61B is provided between the left pulling wire 23L and the relay wire 68 and between the right pulling wire 23R and the relay wire 68, for example.

As a result, in the bending operation lever 45, the response sensitivity to the up bending becomes higher than the response sensitivity to the down bending, and the response sensitivity to the down bending becomes higher than the response sensitivity to the left bending and the right bending. That is, the bending portion 7 is set by having the response sensitivity in three steps in order of the tilting operation to the up direction, the down direction, and the left/right directions of the bending operation lever 45 and is bent to the up direction with the most favorable response.

The aforementioned one direction is not limited to the up direction and the one direction may be the down direction, the left direction or the right direction. That is, the order of the response sensitivity in the three steps is not limited to the up direction, the down direction, and the left/right directions of the bending operation lever 45 described above but can be set as appropriate such as the three steps of the up direction, the left direction, and the down/right directions, the three steps of the up direction, the right direction, and the down/left directions, the three steps of the down direction, the up direction, and the left/right directions and the like.

Figure 14B:
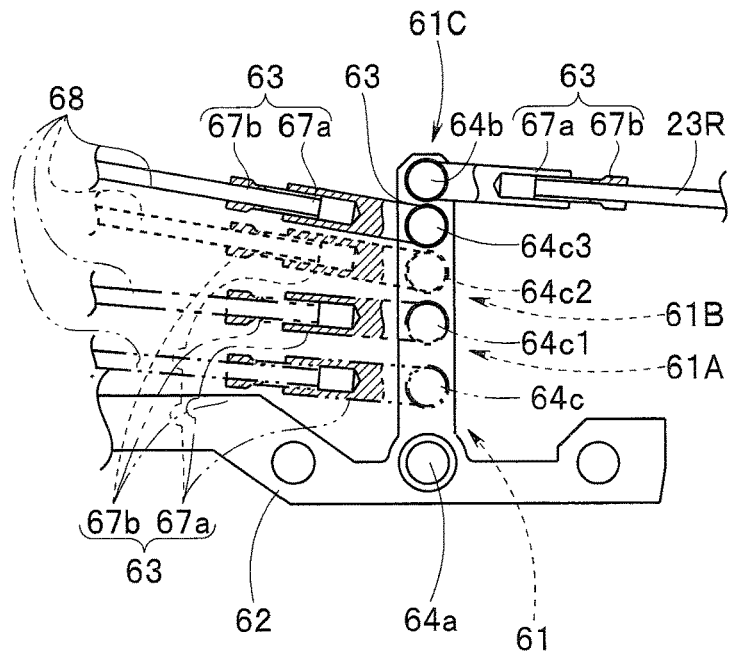
FIG. 14B is a view for explaining a different configuration example of the enlargement link mechanism with a different enlargement rate.

The fourth enlargement link mechanism 61C illustrated in FIG. 14B has a distance from the fulcrum to the power point different from those of the first enlargement link mechanism 61, the second enlargement link mechanism 61A, and the third enlargement link mechanism 61B. More specifically, in the fourth enlargement link mechanism 61C, a position of a third turnable pin 64c3 is disposed closer to the second turnable pin 64b side which is the action point than the position of the third turnable pin 64c2 of the third enlargement link mechanism 61B.

As a result, the distance from the first turnable pin 64a which is the fulcrum of the fourth enlargement link mechanism 61C to the third turnable pin 64c3 which is the power point is larger than the distance from the first turnable pin 64a of the third enlargement link mechanism 61B to the third turnable pin 64c2. Thus, the fourth enlargement rate of the fourth enlargement link mechanism 61C indicated by a solid line is further smaller than the third enlargement rate of the third enlargement link mechanism 61B indicated by a broken line and is the smallest in the four enlargement rates.

Then, the first enlargement link mechanism 61 is provided between the up pulling wire 23U and the relay wire 68, the second enlargement link mechanism 61A is provided between the down pulling wire 23D and the relay wire 68, the third enlargement link mechanism 61B is provided between the left pulling wire 23L and the relay wire 68, and the fourth enlargement link mechanism 61C is provided between the right pulling wire 23R and the relay wire 68, for example.

As a result, in the bending operation lever 45, the response sensitivity to the up bending becomes higher than the response sensitivity to the down bending, the response sensitivity to the down bending becomes higher than the response sensitivity to the left bending, and the response sensitivity to the left bending becomes higher than the response sensitivity to the right bending. That is, the bending portion 7 is set by having the response sensitivity in four steps in order of the tilting operation to the up direction, the down direction, the left direction, and the right direction of the bending operation lever 45 and is bent to the up direction with the most favorable response.

Note that, in the above, the first enlargement link mechanism 61 configured to cause the tilting operation to the up direction in the four directions to take precedence in response is provided between the up pulling wire 23U and the relay wire 68. However, a portion where the first enlargement link mechanism 61 is provided is not limited to the up direction but may be the down direction, the left direction, or the right direction.

Moreover, the order of the response sensitivity in the four steps is not limited to the aforementioned order of the up direction, the down direction, the left direction, and the right direction of the bending operation lever 45, but various settings are possible such as four steps of the up direction, the left direction, the down direction, and the right direction, the four steps of the up direction, the right direction, the down direction, and the left direction or the four steps of the down direction, the up direction, the left direction, and the right direction.

Figure 15:
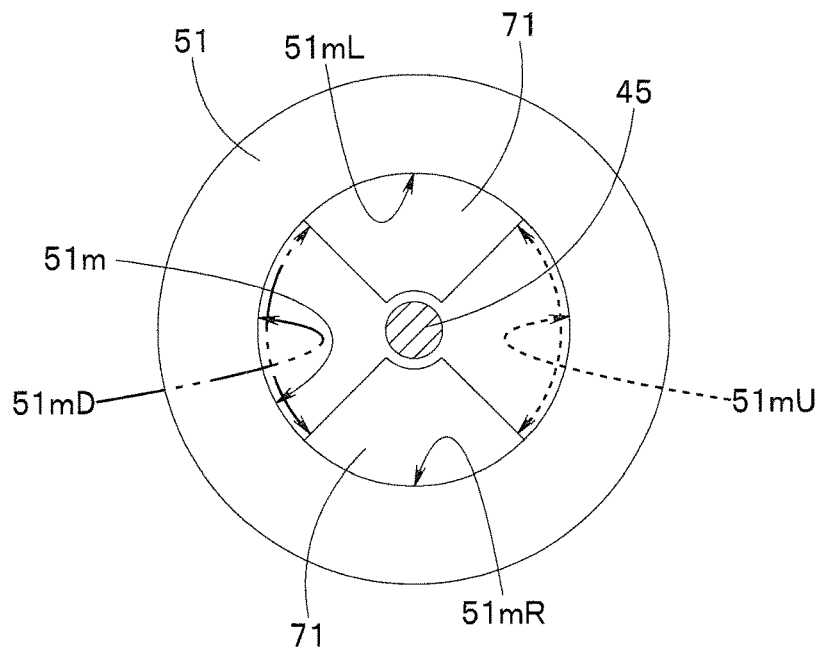
FIG. 15 is a view for explaining an elastic member provided at an opening.

Moreover, an elastic member 71 such as silicon rubber having an elastic force determined in advance and capable of elastic deformation may be disposed on a left tilting surface 51mL and a right tilting surface 51mR of an inner peripheral surface of the opening 51m illustrated in FIGS. 8 and 15 corresponding to the left direction or the right direction, for example, to which the bending operation lever 45 is tilted so that a side surface of the bending operation lever 45 is brought into contact with the elastic member 71 and generates the elastic force when the lever 45 is tilted. As a result, when the bending operation lever 45 is tilted, an operation force amount becomes heavier in the left-right direction than in the up-down direction.

As a result, when the user grasps the grasping portion 31 of the operation portion 3, disposes the thumb of the grasping hand on the finger contact portion 46 and tilts the bending operation lever 45 so as to bend the bending portion 7 to the up direction or to the down direction, if the thumb is slightly moved to the left direction or the right direction, and the bending operation lever 45 is tilted to the left direction or to the right direction, the bending portion 7 can be bent to one direction, that is, to the up direction or to the down direction with a smaller operation force amount.

Note that, in the aforementioned embodiment, the elastic member 71 is provided on the left tilting surface 51mL and the right tilting surface 51mR of the opening 51m so that the operation force amount is made smaller in the up-down direction. However, the direction where the operation force amount is made smaller is not limited to the up-down direction but if the up-down direction is to be made heavier than the left-right direction when the bending operation lever 45 is tilted, for example, the elastic member 71 is provided on an up tilting surface 51mU which is a range indicated by a broken line and a down tilting surface 51mD which is a region which is a range indicated by a two-dot chain line of the opening 51m.

Moreover, if the down direction, the left direction, and the right direction are to be made heavier than the up direction which is one direction when the bending operation lever 45 is tilted, for example, the elastic member 71 is provided on the down tilting surface 51mD, the left tilting surface 51mL, and the right tilting surface 51mR, excluding the up tilting surface 51mU of the opening 51m.

The aforementioned one direction is not limited to the up direction but the one direction may be the down direction, the left direction or the right direction. That is, if the direction where the operation force amount is to be reduced is one direction, the elastic member 71 is disposed on the tilting surfaces of the three directions of the opening 51m different from the direction where the operation force amount is to be reduced. Moreover, if the directions where the operation force amount is to be reduced are two directions, the elastic member 71 is disposed on the tilting surfaces in two directions of the opening 51m different from the two directions where the operation force amount is to be reduced.

Note that, instead of disposing the elastic member 71, a thickness of the bending boot 59 may be set and adjusted as appropriate for each tilting operation direction so that the operation force amount is brought into a desired state.

In the aforementioned embodiment, the distal end portion of the up pulling wire 23U, the distal end portion of the down pulling wire 23D, the distal end portion of the left pulling wire 23L, and the distal end portion of the right pulling wire 23R corresponding to the up, the down, the left, and the right directions, respectively, are fixed to the four wire fixing portions 21 provided around the insertion axis O on the inner periphery of the most distal bending piece 20 as illustrated in FIG. 5.

Then, the bending portion 7 is configured to be bent to the up direction when the up-wire arm portion 54bU is made to swing, and the up pulling wire 23U is mainly pulled/moved with the tilting operation to the up direction of the bending operation lever 45. Moreover, the bending portion 7 is configured to be bent to the down direction when the down-wire arm portion 54bD is made to swing, and the down pulling wire 23D is mainly pulled/moved with the tilting operation to the down direction of the bending operation lever 45. Moreover, the bending portion 7 is configured to be bent to the left direction when the left-wire arm portion 54bL is made to swing, and the left pulling wire 23L is mainly pulled/moved with the tilting operation to the left direction of the bending operation lever 45. Moreover, the bending portion 7 is configured to be bent to the right direction when the right-wire arm portion 54bR is made to swing, and the right pulling wire 23R is mainly pulled/moved with the tilting operation to the right direction of the bending operation lever 45.

However, the bending portion 7 may be bendable to the one direction by pulling/moving the adjacent two pulling wires in the four pulling wires 33U, 33D, 33L, and 33R in accordance with the tilting operation to one direction in the four directions of the bending operation lever 45 and may be actively bendable to all the directions around the insertion axis O including the up, down, left, and right directions.

Figure 16:
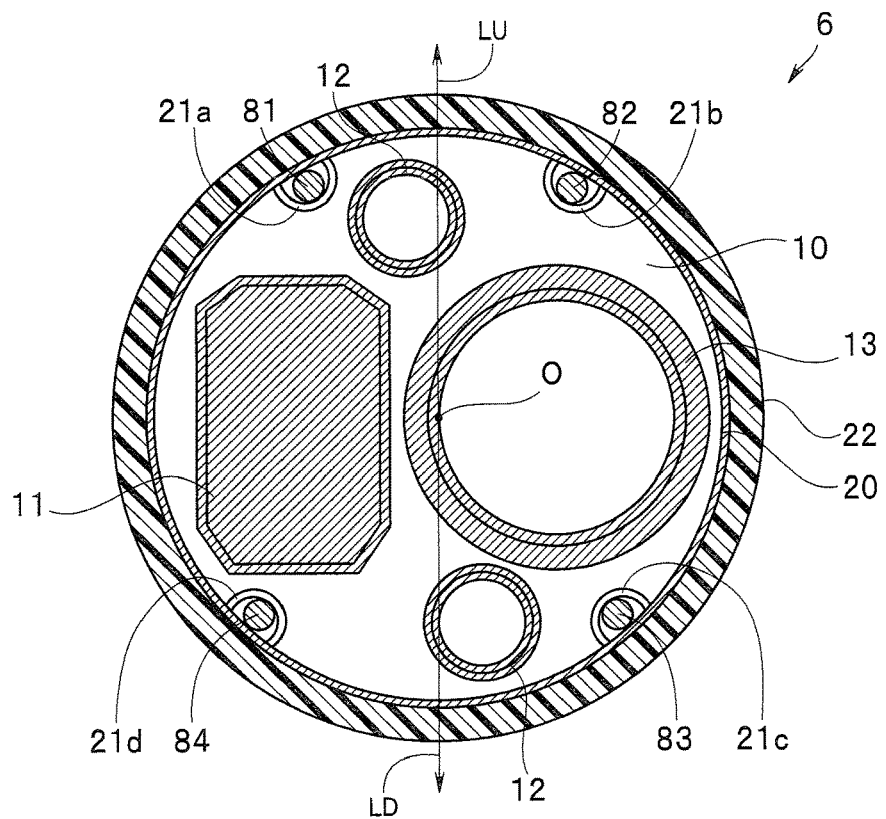
FIG. 16 is a view illustrating a configuration example in which fixation positions of distal end portions of four wires configured to cause a most distal bending piece to bend the bending portion are changed.

Thus, in the embodiment, wire fixing portions 21a and 21b are provided at positions rotated/moved within a range of 30 to 60 degrees to left and right, respectively, around the insertion axis O with a bending up direction line LU of the distal end portion 6 as a reference as illustrated in FIG. 16, while wire fixing portions 21c and 21d are provided at positions rotated/moved within a range of 30 to 60 degrees to left and right, respectively, around the insertion axis O with a bending down direction line LD of the distal end portion 6 as a reference. Distal end portions of pulling wires 81, 82, 83, and 84 are fixed to each of the wire fixing portions 21a, 21b, 21c, and 21d.

The end portions of the pulling wires 81, 82, 83, and 84 extended into the operation portion 3 through the insertion portion 2 are configured to be disposed in wire disposing holes 91h, 92h, 93h, and 94h provided as pulling wire connection portions in four wire arm portions 91, 92, 93, and 94 of a wire pulling member 90 illustrated in FIGS. 17A to 17E, respectively.

The angle between the adjacent straight lines connecting the center of the fixed hole 54h and the center of each of the wire disposing holes 54c is set to 90 degrees in the wire pulling member 54 illustrated in FIG. 10A and the like. Thus, the wire pulling member 54 has a cross shape. On the other hand, the wire pulling member 90 illustrated in FIGS. 17A to 17E has a substantially X-shape. Assuming that an angle formed by the first wire arm portion 91 and the second wire arm portion 92 which is an angle formed by a first straight line L1l connecting a first center c91 of the first wire disposing hole 91h and an intersection P100 of the fixing hole 90h and a second straight line L12 connecting a second center c92 of the second wire disposing hole 92h and the intersection P100, and an angle formed by the third wire arm portion 93 and the fourth wire arm portion 94 which is an angle formed by a third straight line L13 connecting a third center c93 of the third wire disposing hole 93h and the intersection P100 and a fourth straight line L14 connecting a fourth center c94 of the fourth wire disposing hole 94h and the intersection P100 are θ1 and that an angle formed by the first wire arm portion 91 and the fourth wire arm portion 92 which is an angle formed by the first straight line L11 and the fourth straight line 4, and an angle formed by the second wire arm portion 92 and the third wire arm portion 93 which is an angle formed by the second straight line L12 and the third straight line L13 are θ2, the angle θ1 is set to less than 90 degrees which is an angle smaller than the angle θ2.

Figure 17A:
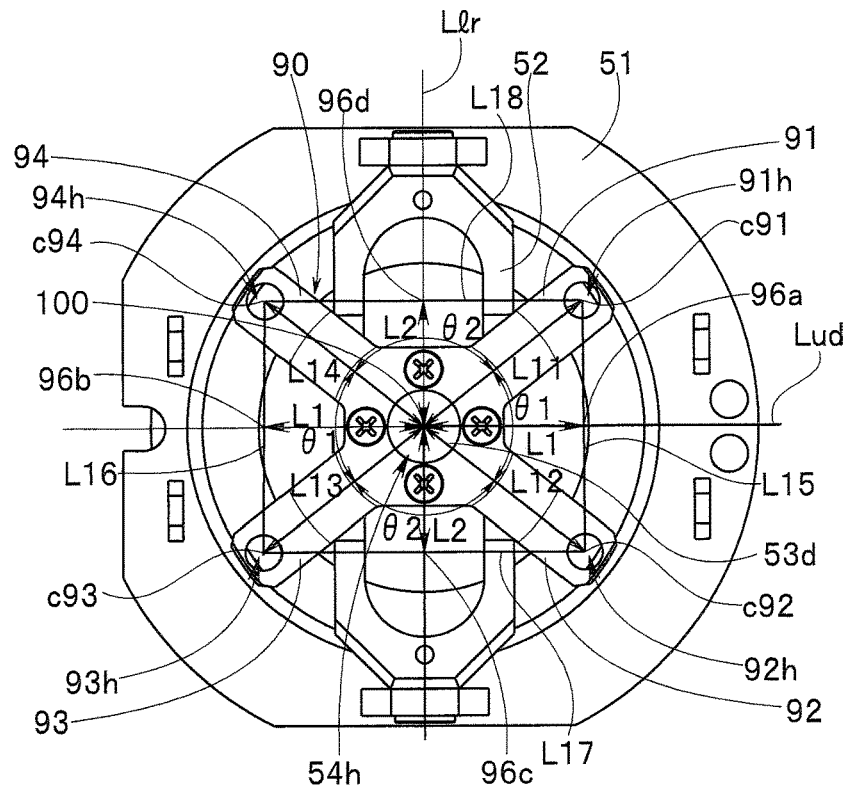
FIG. 17A is a view for explaining a configuration example of the lever tilting angle adjustment mechanism corresponding to the fixation position of the wire distal end portion in FIG. 16.

In FIG. 17A, inter-center distances which are lengths of the first straight line L11, the second straight line L12, the third straight line L13, and the fourth straight line L14 are set to an equal distance. The first center c91 and the second center c92 are provided by facing each other by sandwiching the up-down direction tilting axis Lud, the second center c92 and the third center c93 are provided by facing each other by sandwiching the left-right direction tilting axis Llr, the third center c93 and the fourth center c94 are provided by facing each other by sandwiching the up-down direction tilting axis Lud, and the fourth center c94 and the third center c93 are provided by facing each other by sandwiching the left-right direction tilting axis Llr. The fourth center c94 is faced with the first center c91 with the left-right direction tilting axis Lud sandwiched. An intersection C100 where the up-down direction tilting axis Lud and the left-right tilting axis Llr cross each other matches a center of the fixing portion.

In the embodiment, a first distance starting at the intersection P100 and ending at a first intersection 96a where a straight line L15 connecting the first center c91 and the second center c92 crosses the up-down direction tilting axis Lud and a second distance starting at the intersection P100 and ending at a second intersection 96b where a straight line L16 connecting the third center c93 and the fourth center c94 crosses the up-down direction tilting axis Lud are set to L1, while a third distance starting at the intersection P100 and ending at a third intersection 96c where a straight line L17 connecting the second center c92 and the third center c93 crosses the left-right direction tilting axis Llr and a fourth distance starting at the intersection P100 and ending at a fourth intersection 96d where a straight line L18 connecting the first center c91 and the fourth center c94 crosses the left-right direction tilting axis Llr are set to L2. Here, the distance L1 is set longer than the distance L2 similarly to the aforementioned embodiment.

In the configuration, if the user tilts the bending lever 45 to the up direction by the angle θ, for example, the first wire arm portion 91 and the second wire arm portion 92 adjacent by sandwiching the up-down direction tilting axis Lud similarly swing. As a result, the adjacent first pulling wire 81 and second pulling wire 82 are pulled/moved at the same time by the same distance, and the bending portion 7 is bent to the up direction.

On the other hand, if the user tilts the bending lever 45 to the left direction by the same angle θ, for example, the second wire arm portion 92 and the third wire arm portion 93 adjacent by sandwiching the left-right direction tilting axis Llr similarly swing. As a result, the adjacent second pulling wire 82 and third pulling wire 83 are pulled/moved at the same time. At this time, the second pulling wire 82 and the third pulling wire 83 are pulled/moved by the same distance which is smaller than the distance by which the first pulling wire 81 and the second pulling wire 82 are pulled/moved, and the bending portion 7 is bent to the left direction.

In the embodiment, the pulling amount by which the first pulling wire 81 and the second pulling wire 82 are moved when the bending portion 7 is to be bent to the up direction is larger than the pulling amount by which the second pulling wire 82 and the third pulling wire 83 are pulled when the bending portion 7 is to be bent to the left direction and thus, when the bending operation lever 45 is tilted to the up direction and to the left direction by the same angle θ, for example, similarly to the aforementioned embodiment, a difference is generated between the bending angle to the up direction and the bending angle to the left direction of the bending portion 7, and the up-direction bending angle becomes larger than the left-direction bending angle.

That is, in the embodiment, too, the bending operation lever 45 has the response sensitivity to the up-down bending set higher than the response sensitivity to the left-right bending. Thus, when the bending portion 7 is to be bent to the up-down direction at the bending angle determined in advance similarly to the aforementioned embodiment, the bending operation lever 45 is tilted at the first tilting angle to the up-down direction, while when the bending portion 7 is to be bent to the left-right direction at the same bending angle, the bending operation lever 45 needs to be tilted to the left-right direction at the second tilting angle larger than the first tilting angle. Therefore, the bending portion 7 starts bending by slightly tilting the bending operation lever 45 to the up-down direction, while the bending is not started to the left-right direction unless the bending operation lever 45 is tilted larger than the up-down direction.

As described above, the response sensitivity when the bending operation lever 45 is to be bent in the up-down direction can be made higher than the response sensitivity when the bending operation lever 45 is to be bent in the left-right direction by causing the centers c91, c92, c93, and c94 of each of the wire disposing holes 91h, 92h, 93h, and 94h provided in each of the wire arm portions 91, 92, 93, and 94 of the wire pulling member 90 to be faced by sandwiching the up-down direction tilting axis Lud and the left-right direction tilting axis Llr and then, by setting the first distance starting at the intersection P100 and ending at the first intersection 96a and the second distance ending at the second intersection 96b larger than the third distance starting at the intersection P100 and ending at the third intersection 96c and the fourth distance ending at the fourth intersection 96d.

As a result, similarly to the aforementioned embodiment, when the user grasps the grasping portion 31 of the operation portion 3, disposes the thumb of the grasping hand on the finger contact portion 46, and tilts the bending operation lever 45 so as to bend the bending portion 7 to the up direction or to the down direction, if the thumb is slightly moved to the left direction or the right direction, and the bending operation lever 45 is tilted to the left direction or the right direction, the angle at which the bending portion 7 is bent to the left direction or the right direction is small. Therefore, the bending portion 7 is bent to one direction, that is, to the up direction or to the down direction mainly in response to the tilting operation of the bending operation lever 45 to the up direction or the down direction.

Note that the wire pulling member 90 is not limited to the substantially X-shape but may have a circular shape, a square shape or the like. Moreover, in the aforementioned embodiment, the direction with high response sensitivity is determined to be the up direction and the down direction in advance. However, the direction with high response sensitivity is not limited to the two directions, that is, the up direction and the down direction, and the two directions, that is the left direction and the right direction may be the directions with high response sensitivity.

Figure 17B:
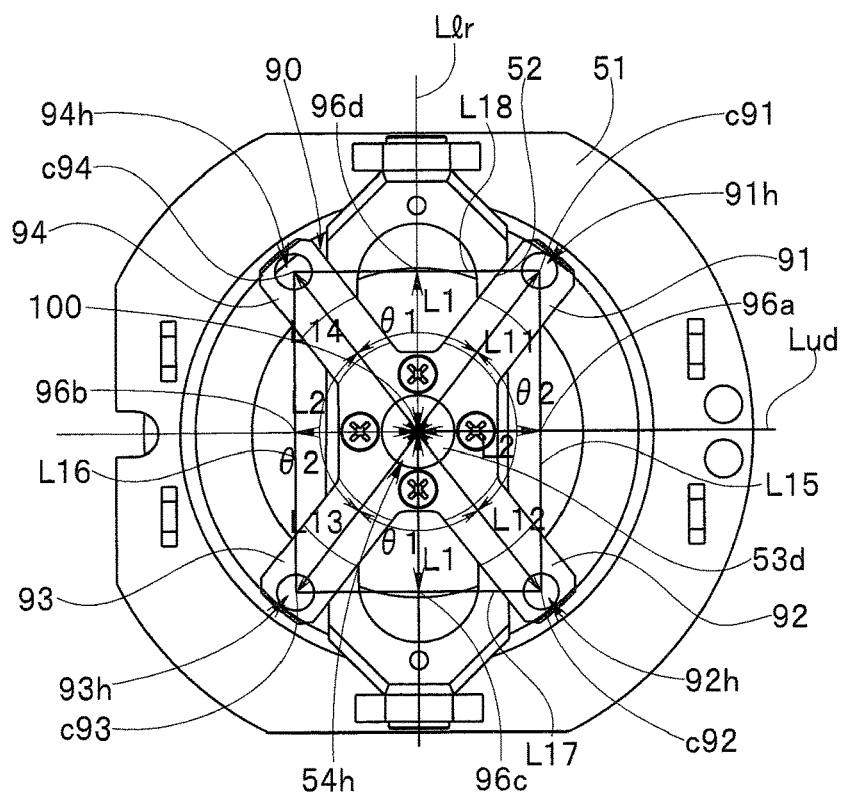
FIG. 17B is a view for explaining another configuration example of the lever tilting angle adjustment mechanism.

The lengths of the first straight line L11, the second straight line L12, the third straight line L13, and the fourth straight line L14 of the wire pulling member 90 illustrated in FIG. 17B are set to an equal distance. In the embodiment, an angle formed by the first wire arm portion 91 and the fourth wire arm portion 94 and an angle formed by the second wire arm portion 92 and the third wire arm portion 93 are set to θ1 less than 90 degrees, and an angle formed by the first wire arm portion 91 and the second wire arm portion 92 and an angle formed by the third wire arm portion 93 and the fourth wire arm portion 94 are set to θ2 larger than θ1.

In the configuration, the third distance starting at the intersection P100 and ending at the third intersection 96c and the fourth distance ending at the fourth intersection 96d are set to L1, while the first distance starting at the intersection P100 and ending at the first intersection 96a and the second distance ending at the second intersection 96b are set to L2.

As a result, the response sensitivity of the bending operation lever 45 to the left bending and the right bending becomes higher than the response sensitivity to the up bending and the down bending. Therefore, similarly to the aforementioned embodiment, when the user grasps the grasping portion 31 of the operation portion 3, disposes the thumb of the grasping hand on the finger contact portion 46, and tilts the bending operation lever 45 so as to bend the bending portion 7 to the left direction or to the right direction, if the thumb is slightly moved to the up direction or the down direction, and the bending operation lever 45 is tilted to the up direction or the down direction, an angle at which the bending portion 7 is bent to the up direction or the down direction is small. Thus, the bending portion 7 is bent to one direction of the left direction or the right direction mainly in response to the tilting operation of the bending operation lever 45 to the left direction or the right direction.

In the above, the direction with high response sensitivity is two directions, that is, the up-down directions or two directions, that is, the left and right directions. However, the direction with high response sensitivity may be one direction or only the up direction may be the direction with high response sensitivity, for example.

Figure 17C:
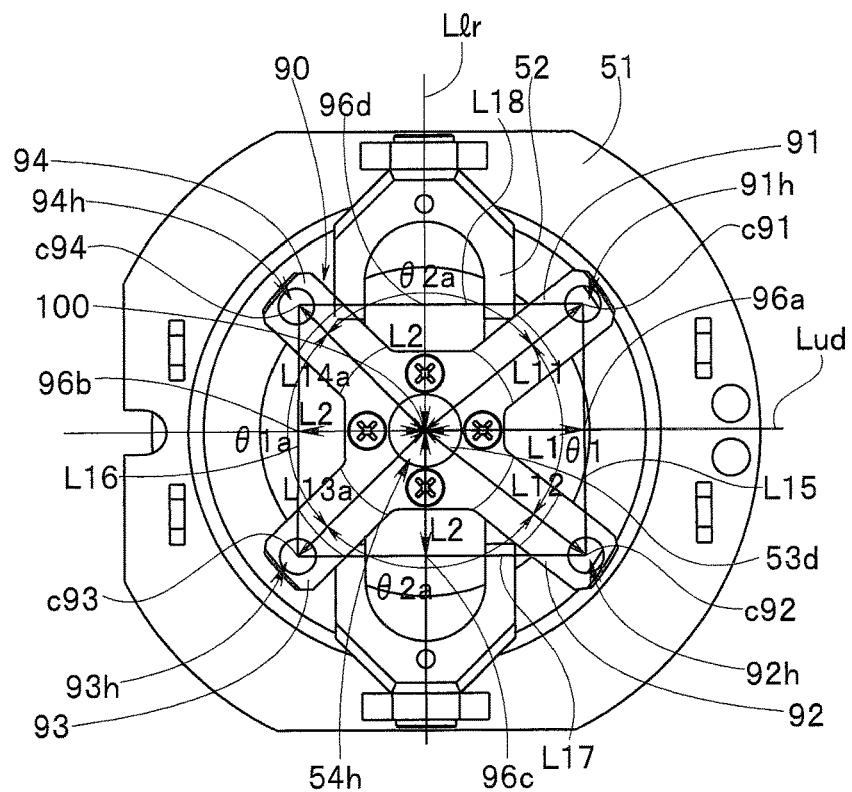
FIG. 17C is a view for explaining a different configuration example of the lever tilting angle adjustment mechanism.

The lengths of the first straight line L11 and the second straight line L12 of the wire pulling member 90 illustrated in FIG. 17C are the same, and the lengths of a third straight line L13a and a fourth straight line L14a are the same. And the lengths of the first straight line L11 and the second straight line L12 are set longer than the lengths of the third straight line L13a and the fourth straight line L14a. Moreover, in the embodiment, the angle formed by the first wire arm portion 91 and the second wire arm portion 92 is θ1, and the angle formed by the third wire arm portion 93 and the fourth wire arm portion 94 is θ1a less than 90 degrees. On the other hand, the angle formed by the second wire arm portion 92 and the third wire arm portion 93 and the angle formed by the fourth wire arm portion 94 and the first wire arm portion 91 are set to θ2a larger than θ1 and θ1a.

In the configuration, the first distance starting at the intersection P100 and ending at the first intersection 96a is set to L1, while the second distance starting at the intersection P100 and ending at the second intersection 96b, the third distance ending at the third intersection 96c, and the fourth distance ending at the fourth intersection 96d are set to L2. As a result, the response sensitivity of the bending operation lever 45 to the up bending becomes higher than the response sensitivity to the down bending, the left bending, and the right bending. Therefore, the bending portion 7 is bent to the up direction mainly in response to the tilting operation to the up direction of the bending operation lever 45.

In the above, the response sensitivity is in two steps, but the response sensitivity may be configured in three steps or four steps.

First, the wire pulling member 90 having the response sensitivity in three steps will be described.

Figure 17D:
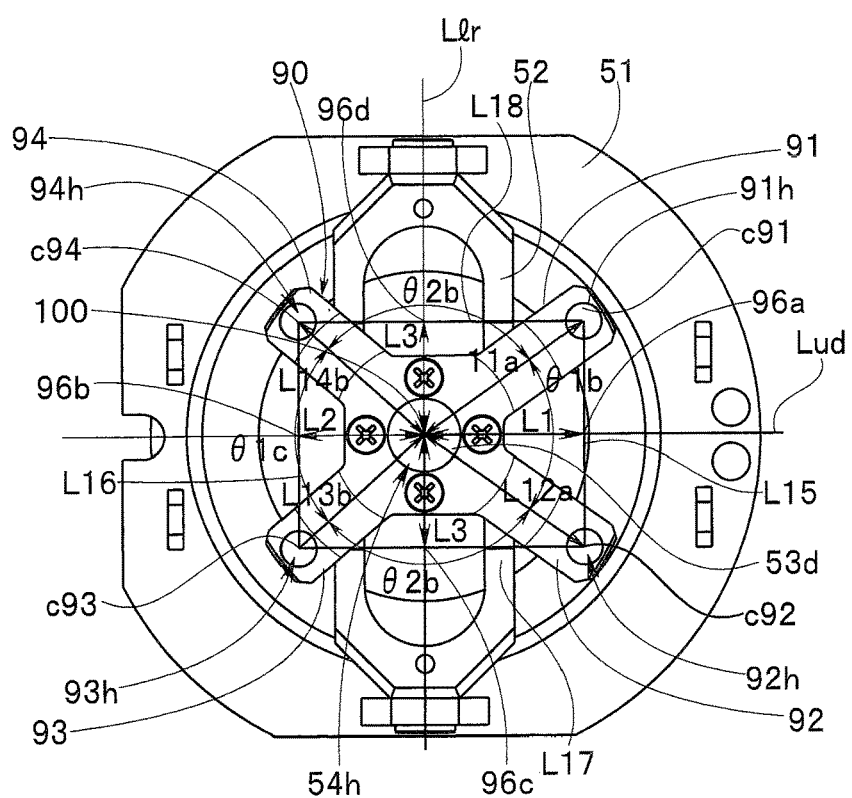
FIG. 17D is a view for explaining still another configuration example of the lever tilting angle adjustment mechanism.

The lengths of a first straight line L11a and a second straight line L12a of the wire pulling member 90 illustrated in FIG. 17D are the same, and the lengths of a third straight line L13b and a fourth straight line L14b are the same. The lengths of the first straight line L11a and the second straight line L12a are set longer than the lengths of the third straight line L13b and the fourth straight line L14b. Moreover, in the embodiment, the angle formed by the first wire arm portion 91 and the second wire arm portion 92 is θ1b less than 90 degrees, and the angle formed by the third wire arm portion 93 and the fourth wire arm portion 94 is θ1c also less than 90 degrees. On the other hand, the angle formed by the second wire arm portion 92 and the third wire arm portion 93 and the angle formed by the fourth wire arm portion 94 and the first wire arm portion 91 are set to θ2b larger than θ1b and θ1c. Note that θ1e is an angle larger than θ1b.

In the configuration, the first distance starting at the intersection P100 and ending at the first intersection 96a is set to L1, the second distance starting at the intersection P100 and ending at the second intersection 96b is set to L2, the third distance starting at the intersection P100 and ending at the third intersection 96c and the fourth distance ending at the fourth intersection 96d are set to L3 shorter than L2. As a result, the response sensitivity of the bending operation lever 45 to the up bending becomes higher than the response sensitivity to the down bending, and the response sensitivity to the down bending becomes higher than the response sensitivity to the left bending and the right bending. That is, the bending portion 7 is set having the response sensitivity in three steps in order of the tilting operation to the up direction, the down direction, and the right/left directions of the bending operation lever 45 and is bent to the up direction with the most favorable response.

Subsequently, the wire pulling member 90 having the response sensitivity in four steps will be described.

Figure 17E:
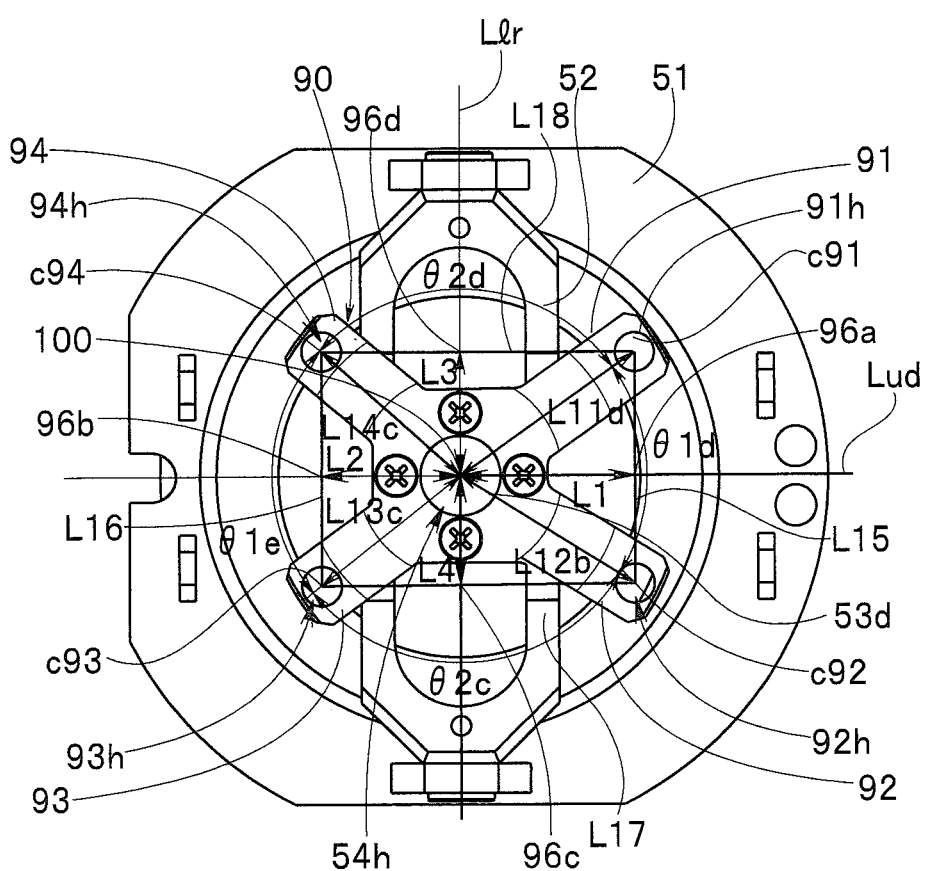
FIG. 17E is a view for explaining a still different configuration example of the lever tilting angle adjustment mechanism.

The lengths of a first straight line L11b and a second straight line L12b of the wire pulling member 90 illustrated in FIG. 17E are the same, and the lengths of a third straight line L13c and a fourth straight line L14c are the same. The lengths of the first straight line L11b and the second straight line L12b are set longer than the lengths of the third straight line L13c and the fourth straight line L14c. Moreover, in the embodiment, the angle formed by the first wire arm portion 91 and the second wire arm portion 92 is θ1d less than 90 degrees, and the angle formed by the third wire arm portion 93 and the fourth wire arm portion 94 is θ1e also less than 90 degrees. On the other hand, the angle formed by the second wire arm portion 92 and the third wire arm portion 93 is θ2c larger than θ1d and θ1e, and the angle formed by the fourth wire arm portion 94 and the first wire arm portion 91 are set to θ2d larger than θ2c. Note that θ1e is an angle larger than θ1d.

In the configuration, the first distance starting at the intersection P100 and ending at the first intersection 96a is set to L1, the second distance starting at the intersection P100 and ending at the second intersection 96b is set to L2, the third distance starting at the intersection P100 and ending at the third intersection 96c is set to L3, and the fourth distance starting at the intersection P100 and ending at the fourth intersection 96d is set to L4 shorter than L3. As a result, the response sensitivity of the bending operation lever 45 to the up bending becomes higher than the response sensitivity to the down bending, the response sensitivity to the down bending becomes higher than the response sensitivity to the left bending, and the response sensitivity to the left bending becomes higher than the response sensitivity to the right bending. That is, the bending portion 7 is set having the response sensitivity in four steps in order of the tilting operation to the up direction, the down direction, the left direction, and the right direction of the bending operation lever 45 and is bent to the up direction with the most favorable response.

Note that the aforementioned one direction is not limited to the up direction and the one direction may be the down direction, the left direction or the right direction. That is, the order of the response sensitivity in the three steps is not limited to the up direction, the down direction, and the left/right directions of the bending operation lever 45 described above, but various settings can be made such as the three steps of the up direction, the left direction, and the down/right directions, the three steps of the up direction, the right direction, and the down/left directions, the three steps of the down direction, the up direction, and the left/right directions direction and the like.

Moreover, in the above, the two directions are a combination of the up direction and the down direction and a combination of the left direction and the right direction. However, the combination of the two directions may be a combination of the up direction and the left direction, a combination of the up direction and the right direction, a combination of the down direction and the left direction or a combination of the down direction and the right direction.

In the embodiment, the combination of the bending angle and the response sensitivity can be set freely depending on a type of the endoscope. If the up-direction bending angle, the down-direction bending angle, the left-direction bending angle, and the right-direction bending angle of the bending portion 7 in the endoscope 1 are made same, for example, a movable range of the bending operation lever only needs to be set small in a direction with high response sensitivity, while the movable range of the bending operation lever only needs to be set large in a direction with low response sensitivity. If the response sensitivity in the up-down direction is set high and the response sensitivity in the left-right direction is set low, for example, in order to set the bending angle in all the directions, that is, the up, the down, the left, and the right directions to 180 degrees, for example, the movable range of the bending operation lever 45 is set small in the up-down direction and wide in the left-right direction. As a result, the bending angles in all the directions, that is, the up, the down, the left, and the right directions can be set same while the bending operation function for allowing bending easily only in a desired direction is provided.

Moreover, if the bending angle in at least one direction in the up-direction bending angle, the down-direction bending angle, the left-direction bending angle, and the right-direction bending angle of the bending portion 7 in the endoscope 1 is made different from the bending angle in another direction, the bending angle in the direction with high response sensitivity only needs to be set large, and the bending angle in the direction with low response sensitivity only needs to be set small. If the response sensitivity in the up-down direction is to be set high and the response sensitivity in the left-right direction is to be set low, for example, the bending angle in the up-down direction is set to 270 degrees, for example, and the bending angle in the left-right direction is set to 180 degrees, for example. As a result, the tilting operation with the movable ranges of the bending operation lever 45 substantially the same in the up-down direction and the left-right direction can be realized.

Note that the present invention is not limited to each of the embodiments described above but is capable of various variations and changes and those variations and changes are also within the technical range of the present invention.

What is claimed is:

1. An endoscope comprising:
   a bending portion bendable in an up direction, a down direction, a left direction, and a right direction,
   a bending operation lever configured to bend the bending portion by being tilted, and
   a wire pulling member provided integrally on the bending operation lever;
   the wire pulling member comprising first, second, third and fourth arms respectively corresponding to the up, down, left and right directions, wherein
   the first arm including an up pulling wire connection portion in which an up pulling wire having one end portion connected to the bending portion and configured to bend the bending portion to the up direction by pulling is disposed, the second arm including a down pulling wire connection portion in which a down pulling wire having one end portion connected to the bending portion and configured to bend the bending portion to the down direction by pulling is disposed, the third arm including a left pulling wire connection portion in which a left pulling wire having one end portion connected to the bending portion and configured to bend the bending portion to the left direction by pulling is disposed, and the fourth arm including a right pulling wire connection portion in which a right pulling wire having one end portion connected to the bending portion and configured to bend the bending portion to the right direction by pulling is disposed, each of the up, down, left and right pulling wire connection portions swing correspondingly to a tilting operation of the bending operation lever,
   the wire pulling member has a center of the up pulling wire connection portion and a center of the down pulling wire connection portion provided on an up-down direction tilting axis and a center of the left pulling wire connection portion and a center of the right pulling wire connection portion provided on a left-right direction tilting axis; and
   an inter-center distance from a center of a fixing portion fixing the bending operation lever and the wire pulling member to the center of the up pulling wire connection portion and an inter-center distance to the center of the down pulling wire connection portion are different from an inter-center distance from the center of the fixing portion to the center of the left pulling wire connection portion and an inter-center distance to the center of the right pulling wire connection portion.

2. The endoscope according to claim 1, wherein
a left-direction bending angle and a right-direction bending angle of the bending portion are smaller than an up-direction bending angle and a down-direction bending angle of the bending portion.

3. The endoscope according to claim 1, wherein
when the bending portion is bent to the left direction or to the right direction, an operation force amount when the bending operation lever is tilted is larger than the operation force amount when the bending operation lever is tilted when the bending portion is bent to the up direction or to the down direction.

4. An endoscope comprising:
   a bending portion bendable in an up direction, a down direction, a left direction, and a right direction,
   a bending operation lever configured to bend the bending portion by being tilted, and
   a wire pulling mechanism provided integrally on the bending operation lever the wire pulling mechanism comprising a wire pulling member having first, second, third and fourth arms respectively corresponding to the up, down, left and right directions;
   the first arm including a first pulling wire connection portion in which a first pulling wire having one end portion connected to the bending portion is disposed, the second arm including a second pulling wire connection portion in which a second pulling wire provided to oppose the first pulling wire connection portion and having one end portion connected to the bending portion is disposed, the third arm including a third pulling wire connection portion in which a third pulling wire provided having one end portion connected to the bending portion is disposed, and the fourth arm including a fourth pulling wire connection portion in which a fourth pulling wire provided to oppose the third pulling wire connection portion and having one end portion connected to the bending portion is disposed;
   the wire pulling mechanism is configured such that:
   a first distance starting at a center of a fixing portion fixing the bending operation lever and the wire pulling member and ending at a first intersection between a straight line connecting a center of the first pulling wire connection portion and a center of the second pulling wire connection portion and the up-down direction tilting axis;
   a second distance starting at the center of the fixing portion and ending at a second intersection between a straight line connecting a center of the third pulling wire connection portion and a center of the fourth pulling wire connection portion and the up-down direction tilting axis;
   a third distance starting at the center of the fixing portion and ending at a third intersection between a straight line connecting the center of the second pulling wire connection portion and the center of the third pulling wire connection portion and the left-right direction tilting axis; and
   a fourth distance starting at the center of the fixing portion and ending at a fourth intersection between a straight line connecting the center of the fourth pulling wire connection portion and the center of the first pulling wire connection portion and the left-right direction tilting axis; and the first distance and the second distance are different from the third distance and the fourth distance.

5. An endoscope comprising:
a bending portion bendable in an up direction, a down direction, a left direction, and a right direction,
a bending operation lever configured to bend the bending portion by being tilted, and
a wire pulling mechanism provided integrally on the bending operation lever and including a link, the link being configured to have a first tilting angle at which the bending operation lever is tilted in order to bend the bending portion to at least one direction of the up, down, left and right directions by a predetermined bending angle and a second tilting angle at which the bending operation lever is tilted in order to bend the bending portion in a direction different from the at least one direction by the predetermined bending angle to different angles when the bending operation lever is tilted so as to bend the bending portion, wherein
the link is provided in a middle portion of a wire and configured to enlarge/convert a pulling distance of the wire generated by a tilting operation of the bending operation lever.

6. The endoscope according to claim 5, wherein
a proximal end portion of an up-direction pulling wire or a down-direction pulling wire having a distal end portion fixed to a most distal bending piece and another end portion of a relay wire in which one end portion is disposed in a wire connection portion of the bending operation lever are connected through the wire pulling amount enlargement mechanism.

7. The endoscope according to claim 5, wherein
the link includes a first enlargement link mechanism having a first enlargement rate and a second enlargement link mechanism having a second enlargement rate;
the first enlargement link mechanism having the first enlargement rate larger than the second enlargement rate is provided between a proximal end portion of the up-direction pulling wire or the down-direction pulling wire and the other end portion of the relay wire having one end portion disposed in an up-direction wire connection portion or a down-direction wire connection portion of the bending operation lever; and
the second enlargement link mechanism having the second enlargement rate is provided between a proximal end portion of the left-direction pulling wire or the right-direction pulling wire and the other end portion of the relay wire having one end portion disposed in a left-direction wire connection portion or a right-direction wire connection portion of the bending operation lever.

8. An endoscope comprising:
a bending portion bendable in first and second directions;
a bending operation lever configured to bend the bending portion in the first and second directions by being tilted;
first and second lever arms each connected at least indirectly to the bending operation lever;
first and second bending wires respectively corresponding to the first and second directions, a first end of the first bending wire being connected to the first lever arm at a first connection point, a first end of the second bending wire being connected to the second lever arm at a second connection point, and a second end of each of the first and second bending wires being connected to the bending portion;
wherein a first moment arm from a first fulcrum of the first lever arm to the first connection point is greater than a second moment arm from a second fulcrum of the second lever arm to the second connection point.

9. The endoscope of claim 8, wherein:
the first and second lever arms being directly connected to an end of the bending operation lever;
the first fulcrum and the second fulcrum are a common fulcrum; and
a first distance from the common fulcrum to the first connection point is greater than a second distance from the common fulcrum to the second connection point.

10. The endoscope of claim 8, wherein:
the bending portion is further bendable in third and fourth directions;
the bending operation lever is further configured to bend the bending portion in the third and fourth directions by being tilted;
further comprising third and fourth lever arms corresponding to the third and fourth directions, respectively;
further comprising third and fourth bending wires corresponding to the third and fourth directions, respectively, a first end of the third bending wire being connected to the third lever arm at a third connection point, a first end of the fourth bending wire being connected to the fourth lever arm at a fourth connection point and a second end of each of the third and fourth bending wires being connected to the bending portion;
the first, second, third and fourth lever arms each being directly connected to an end of the bending operation lever to rotate about a common fulcrum; and
at least a first distance from the common fulcrum to the first connection point is greater than one or more of a second distance from the common fulcrum to the second connection point, a third distance from the common fulcrum to the third connection point or a fourth distance from the common fulcrum to the fourth connection point.

11. The endoscope of claim 10, wherein:
the first and second directions correspond to up and down directions;
the third and fourth directions correspond to left and right directions; and
the first and second distances are each greater than the third and fourth distances.

12. The endoscope of claim 10, wherein:
the first and second directions correspond to up and down directions;
the third and fourth directions correspond to left and right directions; and
the third and fourth distances are each greater than the first and second distances.

13. The endoscope of claim 10, wherein:
the first and second directions correspond to up and down directions, respectively;
the third and fourth directions correspond to left and right directions; and
the first distance is greater than each of the second, third and fourth distances.

14. The endoscope of claim 10, wherein:
the first and second directions correspond to up and down directions, respectively;

the third and fourth directions correspond to left and right directions; and the first distance is greater than the second distance and the second distance is greater than each of the third and fourth distances.

15. The endoscope of claim 10, wherein:

the first and second directions correspond to up and down directions, respectively;

the third and fourth directions correspond to left and right directions, respectively; and the first distance is greater than the second distance, the second distance is greater than the third distance and the third distance is greater than the fourth distance.

16. The endoscope of claim 8, further comprising first and second relay wires respectively corresponding to the first and second bending wires;

wherein a first end of the first relay wire is configured to move with movement of the bending operation lever and a first end of the second relay wire is configured to move with movement of the bending operation lever;

the first lever arm being at least indirectly connected to an operation portion of the endoscope to rotate about the first fulcrum and a second end of the first relay wire is connected to the first lever arm at a first relay point;

the second lever arm being at least indirectly connected to the operation portion of the endoscope to rotate about the second fulcrum and a second end of the second relay wire is connected to the second lever arm at a second relay point;

a first distance from the first fulcrum to the first connection point is greater than a second distance from the first fulcrum to the first relay point;

a third distance from the second fulcrum to the second connection point is greater than a fourth distance from the second fulcrum to the second relay point; and the first distance is greater than the third distance.

* * * * *